(12) United States Patent
Burstein et al.

(10) Patent No.: US 8,414,653 B2
(45) Date of Patent: Apr. 9, 2013

(54) KNEE PROSTHESIS SYSTEM WITH AT LEAST A FIRST TIBIAL PORTION ELEMENT (A TIBIAL INSERT OR TIBIAL TRIAL) AND A SECOND TIBIAL PORTION ELEMENT (A TIBIAL INSERT OR TIBIAL TRIAL), WHEREIN EACH OF THE FIRST TIBIAL PORTION ELEMENT AND THE SECOND TIBIAL PORTION ELEMENT HAS A DIFFERENT SLOPE

(75) Inventors: Albert Burstein, Sarasota, FL (US); Laurent Angibaud, Gainesville, FL (US); Andrea Hayes, Gainesville, FL (US); David Covall, Atlanta, GA (US); Jay Mabrey, Dallas, TX (US); Bernard Stulberg, Chagrin Falls, OH (US); Gary Miller, Gainesville, FL (US); C. Michael Mauldin, Lake City, FL (US)

(73) Assignee: Exactech, Inc., Gainesville, FL (US)

( * ) Notice: Subject to any disclaimer, the term of this patent is extended or adjusted under 35 U.S.C. 154(b) by 403 days.

(21) Appl. No.: 12/368,861

(22) Filed: Feb. 10, 2009

(65) Prior Publication Data
US 2009/0204222 A1    Aug. 13, 2009

Related U.S. Application Data

(60) Provisional application No. 61/027,721, filed on Feb. 11, 2008, provisional application No. 61/098,076, filed on Sep. 18, 2008.

(51) Int. Cl.
*A61F 2/38* (2006.01)

(52) U.S. Cl.
USPC .................... 623/20.32; 623/20.34

(58) Field of Classification Search .............. 623/20.14, 623/20.15, 20.21, 20.31, 20.36
See application file for complete search history.

(56) References Cited

U.S. PATENT DOCUMENTS

| | | | | |
|---|---|---|---|---|
| 4,936,853 A | * | 6/1990 | Fabian et al. ............. | 623/20.15 |
| 5,702,458 A | * | 12/1997 | Burstein et al. ........... | 623/20.31 |
| 5,702,464 A | * | 12/1997 | Lackey et al. ............. | 623/20.32 |
| 5,871,546 A | * | 2/1999 | Colleran et al. .......... | 623/20.28 |
| 5,997,577 A | | 12/1999 | Herrington et al. | |

(Continued)

FOREIGN PATENT DOCUMENTS

WO    2009/102725 A2    8/2009

OTHER PUBLICATIONS

Sigma or Reference Chart, DePuy Orthopedics, Inc. 2007.*

(Continued)

*Primary Examiner* — Thomas J Sweet
*Assistant Examiner* — Brian Dukert
(74) *Attorney, Agent, or Firm* — Greenberg Traurig, LLP

(57) ABSTRACT

One embodiment of the present invention relates to a knee prosthesis system with at least a first tibial portion element (a tibial insert or a tibial insert trial) and a second tibial portion element (a tibial insert or a tibial insert trial), wherein each of the first tibial portion element and the second tibial portion element has a different slope. Another embodiment of the present invention relates to a method of implanting a knee prosthesis, wherein the method utilizes at least a first tibial portion element (a tibial insert or a tibial insert trial) and a second tibial portion element (a tibial insert or a tibial insert trial), wherein each of the first tibial portion element and the second tibial portion element has a different slope.

18 Claims, 23 Drawing Sheets

U.S. PATENT DOCUMENTS

| | | |
|---|---|---|
| 2004/0225368 A1 | 11/2004 | Plumet et al. |
| 2005/0027365 A1* | 2/2005 | Burstein et al. ............ 623/20.32 |
| 2005/0171604 A1* | 8/2005 | Michalow .................. 623/14.12 |
| 2005/0197708 A1 | 9/2005 | Stone et al. |
| 2006/0111790 A1* | 5/2006 | Dietz ......................... 623/20.32 |
| 2006/0190087 A1* | 8/2006 | O'Connor et al. ......... 623/20.33 |
| 2006/0241634 A1 | 10/2006 | Tuttle et al. |
| 2006/0247646 A1 | 11/2006 | Bihary et al. |

OTHER PUBLICATIONS

J. Bellemans, The influence of tibial slope on maximal flexion after total knee arthroplasty, 2005 13:193-196, Knee Surg Sports Traumatol Arthrosc.*

International Search Report from International Application No. PCT/US09/33685 dated May 26, 2009.

* cited by examiner

1: SIZE

2: THICKNESS

3: POSTERIOR SLOPE

1: SIZE

2: THICKNESS

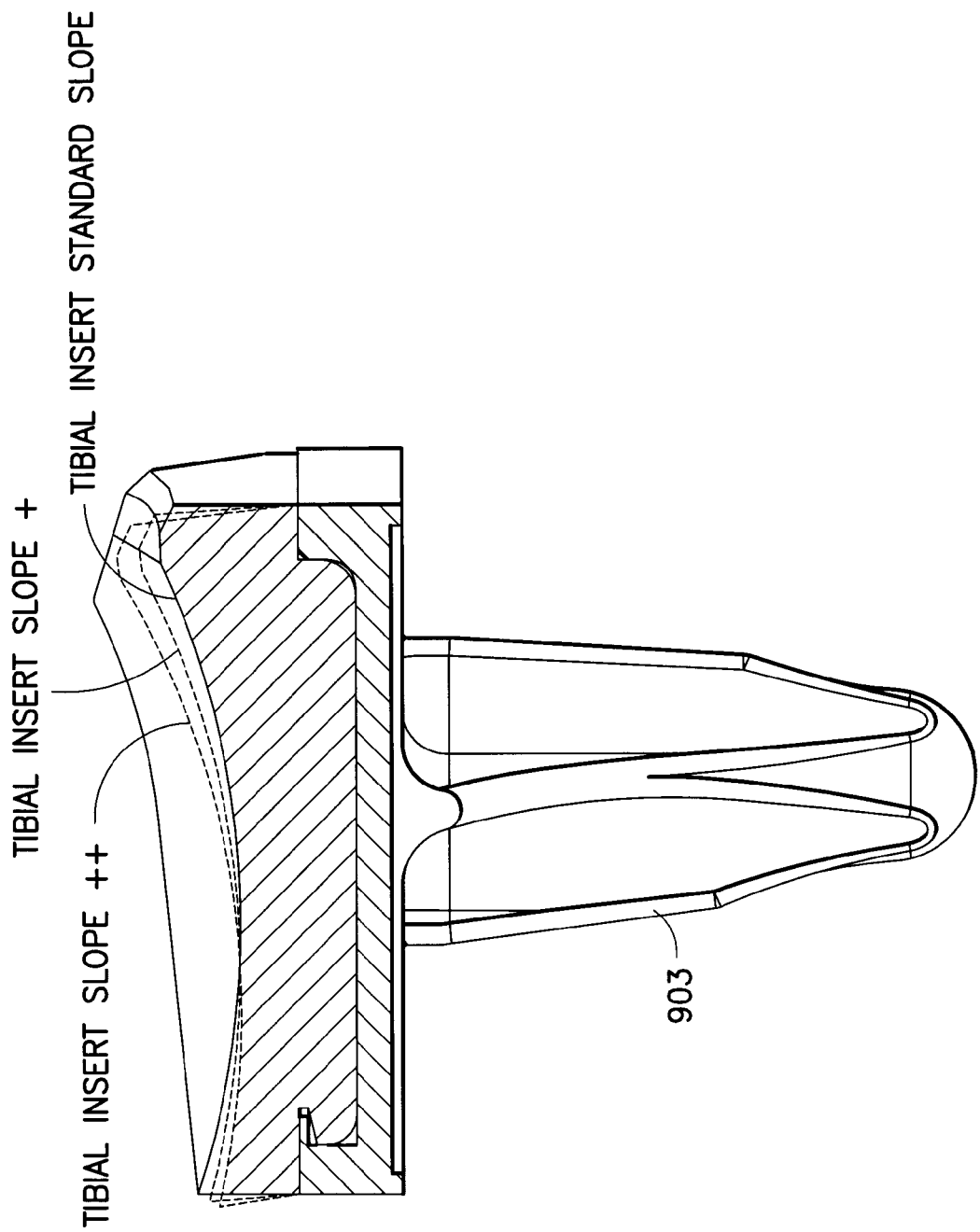

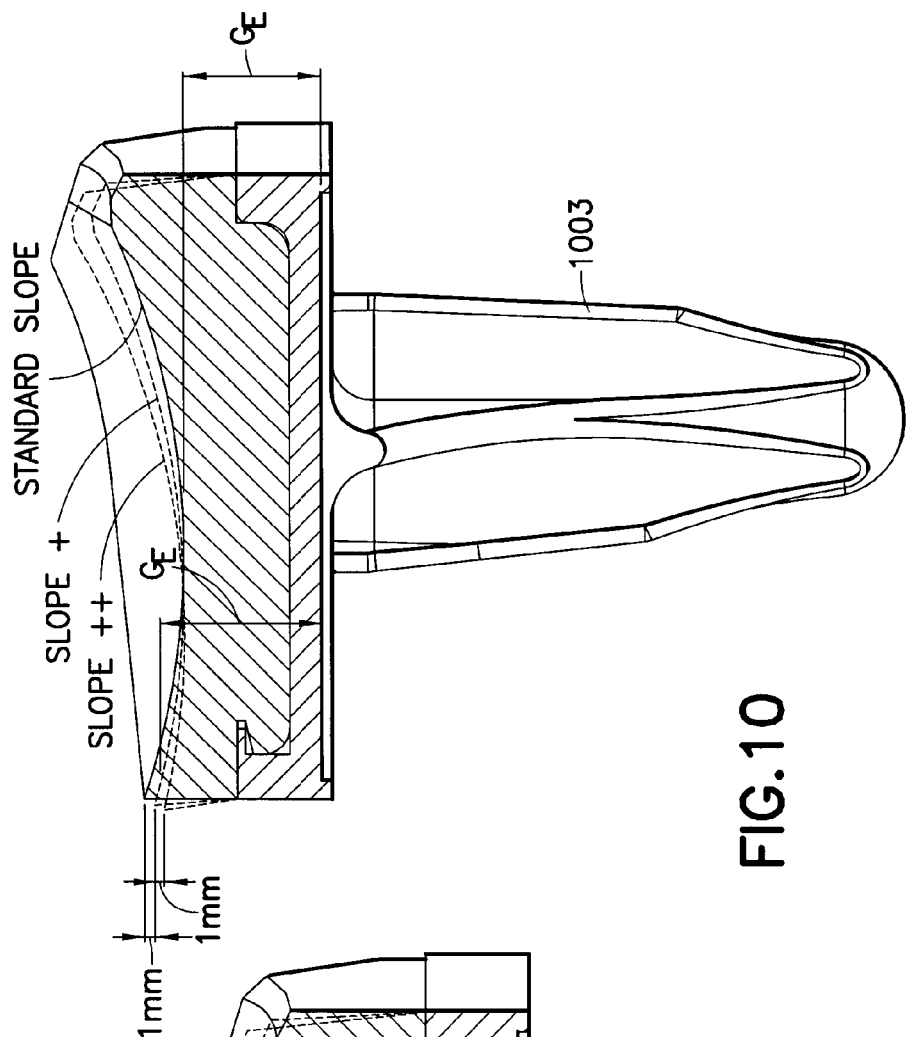
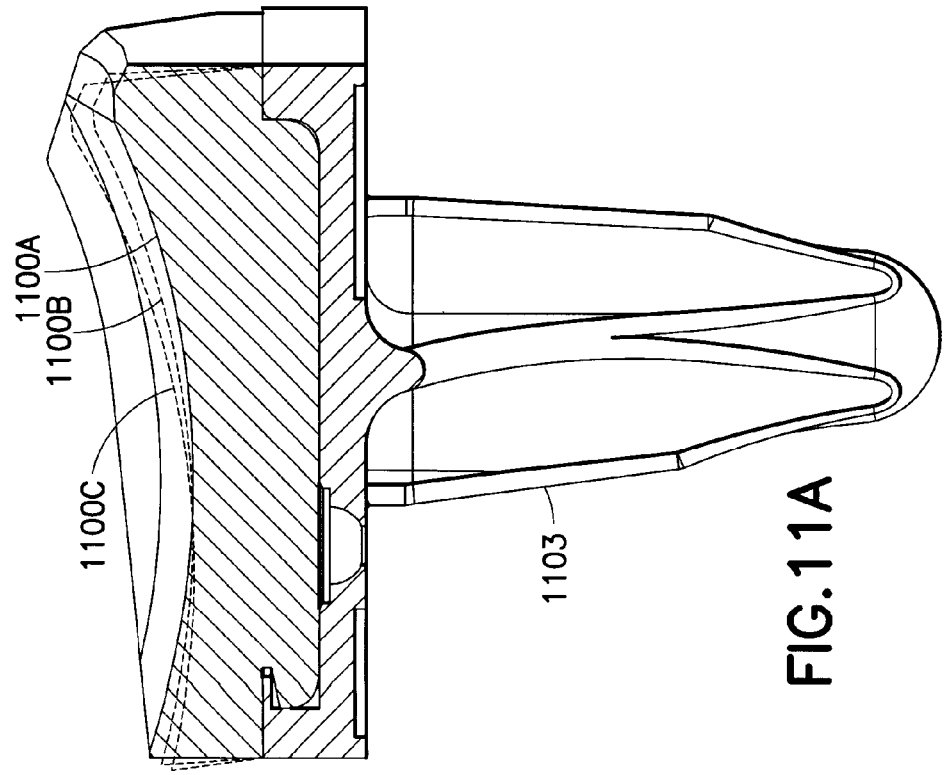

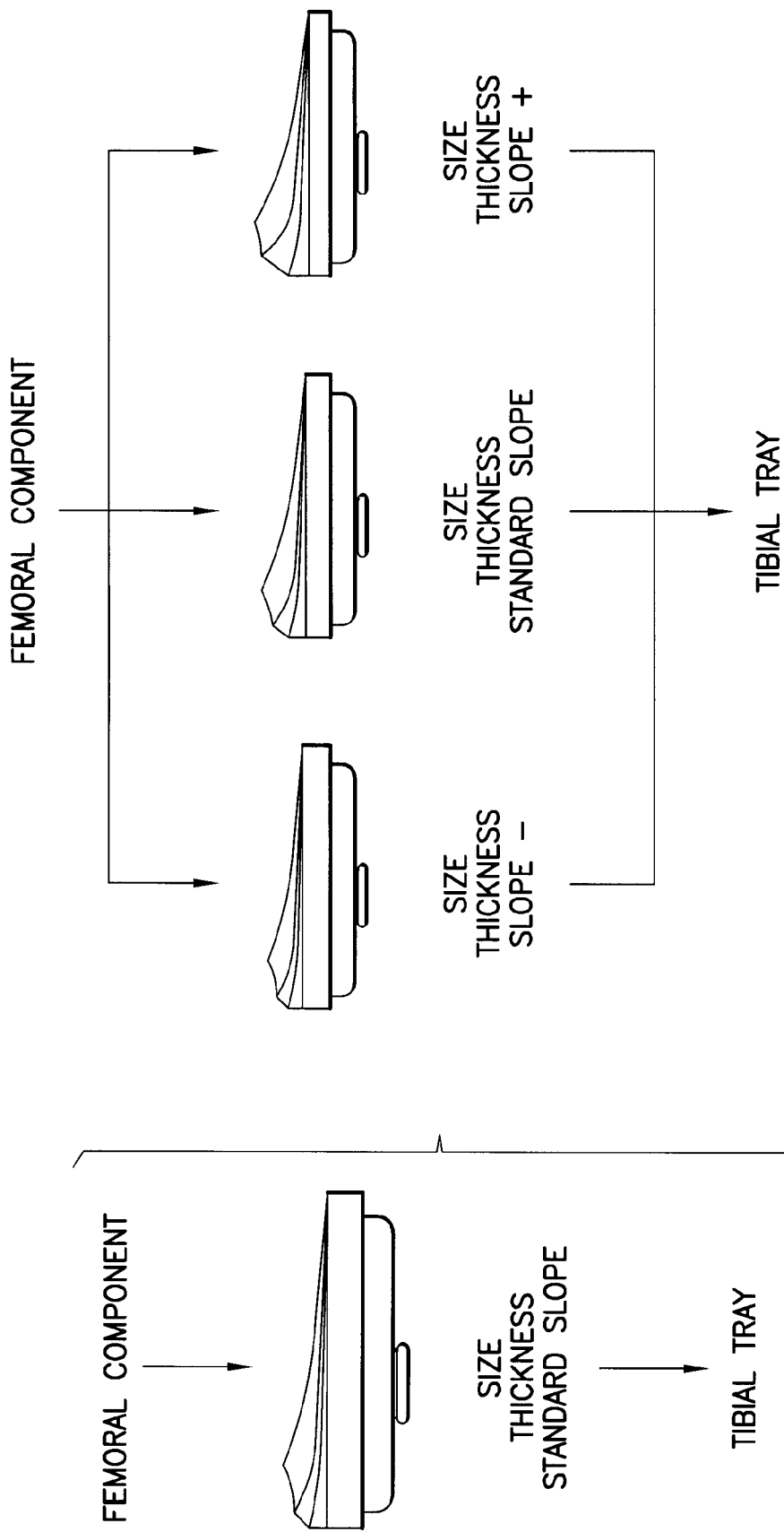

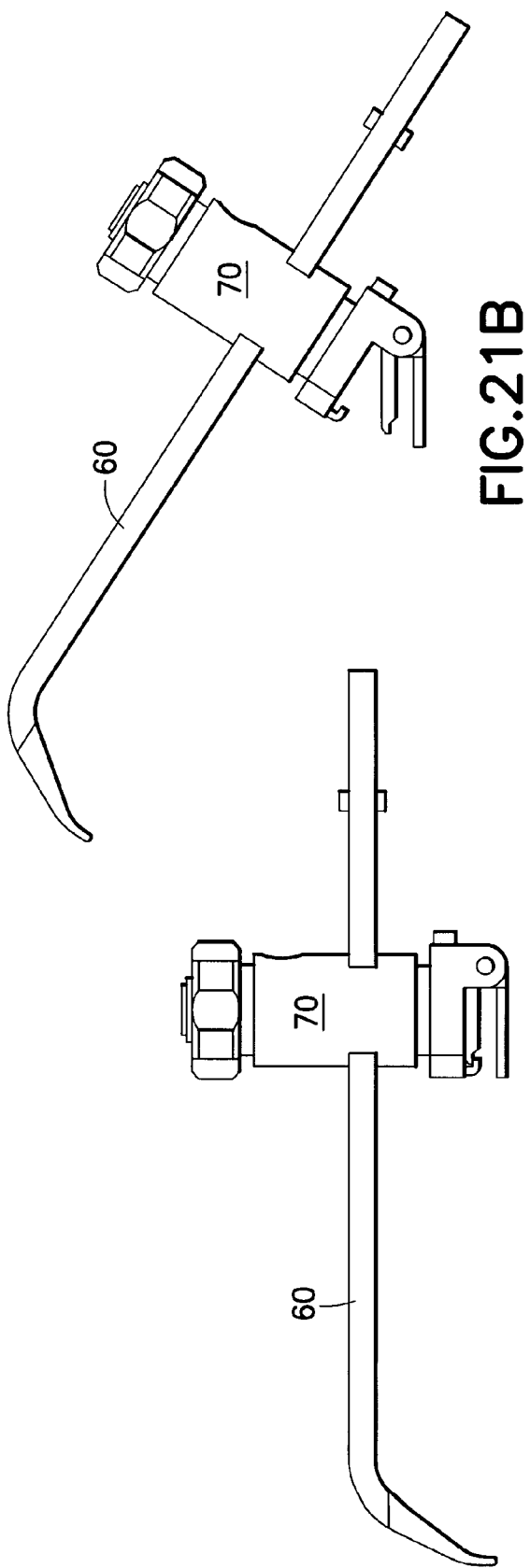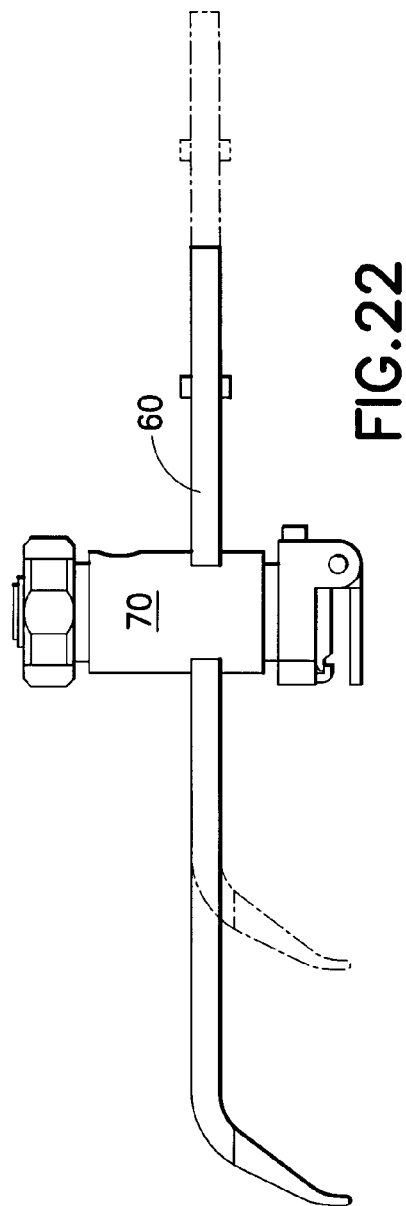

KNEE PROSTHESIS SYSTEM WITH AT LEAST A FIRST TIBIAL PORTION ELEMENT (A TIBIAL INSERT OR TIBIAL TRIAL) AND A SECOND TIBIAL PORTION ELEMENT (A TIBIAL INSERT OR TIBIAL TRIAL), WHEREIN EACH OF THE FIRST TIBIAL PORTION ELEMENT AND THE SECOND TIBIAL PORTION ELEMENT HAS A DIFFERENT SLOPE

RELATED APPLICATIONS

This application claims the benefit of U.S. Provisional Application Ser. No. 61/027,721, filed Feb. 11, 2008. This application also claims the benefit of U.S. Provisional Application Ser. No. 61/098,076, filed Sep. 18, 2008. Each of the aforementioned applications is incorporated herein by reference in its entirety.

FIELD OF THE INVENTION

FIG. 1 shows a sagittal cross-sectional view of a tibial portion 101 of a total knee arthroplasty ("TKA") prosthesis according to one embodiment of the present invention (a corresponding femoral portion of such a total knee arthroplasty prosthesis is not shown in this view). This tibial portion of a total knee arthroplasty prosthesis comprises the following two elements: a tibial tray 103 and a tibial insert 105. The tibial insert 105 includes a first surface (an articular surface 109) configured to interface with a femoral component (not shown).The tibial insert 105 also includes a second surface 107 configured to interface with the tibial tray 103.

A goal of a total knee arthroplasty is to function as a normal knee and in this regard the following two parameters are believed to be important in achieving this goal: appropriate dimensioning of the prosthesis (i.e., having the prosthesis match the morphology of the patient's knee); and appropriate orientation of the prosthesis (e.g., having the centerline of the prosthesis replicate the anatomical centerline).

With regard to dimensioning, one parameter is size (tibial inserts are typically available in several sizes to ensure appropriate coverage of the knee after the proximal tibial cut is made). For the purposes of describing and claiming the present invention, the term "size" is intended to refer to the overall dimension of the tibial insert (or tibial insert trial) in the transverse plane (see $D_1$ of tibial insert 205 of FIG. 2A and $D_2$ of tibial insert 205 of FIG. 2B).

Further, and again with regard to dimensioning, another parameter is thickness (tibial inserts are typically available in several thicknesses to appropriately adjust the gap between the femur and the tibia). For the purposes of describing and claiming the present invention, the term "thickness" is intended to refer to the height of the tibial insert (or tibial insert trial) measured between: (a) the surface configured to interface with a tibial tray; and (b) a low point on the articular surface of the tibial insert (or tibial insert trial)—that is the surface of the tibial insert (or insert trial) configured to interface with a femoral component (see FIG. 3, showing thickness T between the articular surface 309 and tibial tray interface surface 307 (this FIG. 3 shows tibial insert 305 alone (that is, without a tibial tray))).

With regard now to orientation of the tibial portion of the prosthesis, three rotations defining the orientation of the of the tibial portion of the prosthesis (that is, the tibial insert and/or the tibial tray) are typically measured by the surgeon during preparation of the proximal tibia: (a) axial rotation (i.e., the rotation around axis Z—see, e.g., FIGS. 2C-2E); (b) Varus/Valgus angle (i.e., the rotation around axis Y—see, e.g., 2C and 2E); and (c) posterior tibial slope (i.e., the rotation around axis X) (see, e.g., FIGS. 2C, 2D and 4). It is believed that the first two (i.e., axial rotation and VV angle) have been relatively easy to reproduce, but that the third (i.e., posterior tibial slope) has been relatively difficult to reproduce.

In this regard, one embodiment of the present invention relates to a knee prosthesis system with at least a first tibial portion element (a tibial insert or a tibial insert trial) and a second tibial portion element (a tibial insert or a tibial insert trial), wherein each of the first tibial portion element and the second tibial portion element has a different slope.

Another embodiment of the present invention relates to a method of implanting a knee prosthesis, wherein the method utilizes at least a first tibial portion element (a tibial insert or a tibial insert trial) and a second tibial portion element (a tibial insert or a tibial insert trial), wherein each of the first tibial portion element and the second tibial portion element has a different slope.

As mentioned, in one example, each of the first tibial portion element and the second tibial portion element may be a tibial insert trial (e.g., for use in determining the proper tibial inert to be implanted).

Further, as mentioned, in another example, each of the first tibial portion element and the second tibial portion element may be a tibial insert (one of such tibial inserts ultimately being implanted for a given total knee arthroplasty procedure).

For the purposes of describing and claiming the present invention (and with reference, for example, to FIG. 5), the term "slope" (in the context of a tibial insert or a tibial insert trial) is intended to refer to refer to the angle formed by: (a) a planar portion of a back surface of the tibial portion element (e.g., a planar portion of a tibial tray interface surface of a tibial insert or tibial trial—see callout number 501); and (b) a line connecting: (i) a highest point of the articular surface of the tibial insert or tibial insert trial at an anterior end of the tibial insert or tibial insert trial (see callout number 505); and (ii) a highest point of the articular surface of the tibial insert or tibial insert trial at a posterior end of the tibial insert or tibial insert trial (see callout number 503).

BACKGROUND OF THE INVENTION

Both posterior stabilized (PS) and cruciate retaining (CR) total knee replacement systems have demonstrated high rates of survivorship, high clinical knee scores and high patient satisfaction scores over the last few decades. However, CR total knees sometimes exhibit more varied kinematics and diminished range of motion (ROM) than similar PS knees. One known cause of this is a posterior cruciate ligament (PCL) that does not optimally work with the tibial insert, allowing for paradoxical femoral anterior translation in flexion and impingement between the posterior lip of the tibial insert and the posterior femur. This appears to be related to difficulty obtaining optimal postoperative PCL function.

To achieve full (or nearly full) PCL function, a number different surgical techniques have been suggested. These include increasing the slope of the proximal tibial resection, recession of the PCL along its tibial attachment, and resection of additional posterior femoral bone. Each of these approaches can have negative consequences for PCL function and CR total knee replacement performance.

For example, if the PCL is found to be too tight, the surgeon can reduce its tension by re-cutting the proximal tibia with an increased posterior tibial slope. Increasing the slope of the proximal tibial resection can damage the PCL (and/or the tibial PCL attachment), because the re-cut can be distal to the tibial PCL attachment (see FIG. 6).

BRIEF DESCRIPTION OF THE DRAWINGS

FIG. 9A shows an embodiment of the present invention in sagittal cross-section (three example tibial insert slopes are shown in this view (tibial tray 903 is also shown in this view).

FIG. 10 shows an embodiment of the present invention in sagittal cross-section (three example tibial insert slopes are shown in this view (tibial tray 1003 is also shown in this view).

FIGS. 11A-11D shows certain detail regarding three example tibial insert slopes (tibial tray 1103 is also shown in this view).

FIG. 12A is a diagram related to showing that conventional total knee replacement systems typically utilize tibial inserts that vary according to two parameters, size (e.g., from 1 to 5) and the thickness (e.g., from 9 mm to 15 mm).

FIG. 12B is a diagram related to showing how various embodiments of the present invention may provide for an optimum reproduction of knee joint kinematics by adding a third parameter—posterior tibial slope (in addition to the conventional size and thickness parameters).

FIG. 14 is a side view (in partial phantom); and FIG. 15 is a perspective view (in partial phantom)—this view of FIG. 15 also shows a goniometer)).

FIGS. 21A and 21B shows the PCL stylus (and associated instrumentation) of FIG. 20 (wherein the view of FIG. 21A shows the stylus and body in a first orientation relative to a mounting element and the view of FIG. 21B shows the stylus and body in a second, pivoted orientation relative to a mounting element).

FIG. 22 shows the PCL stylus (and associated instrumentation) of FIG. 20 (wherein the view of FIG. 22 shows the translation (in this case, left and right across the page) of the stylus.

Figure 2A:
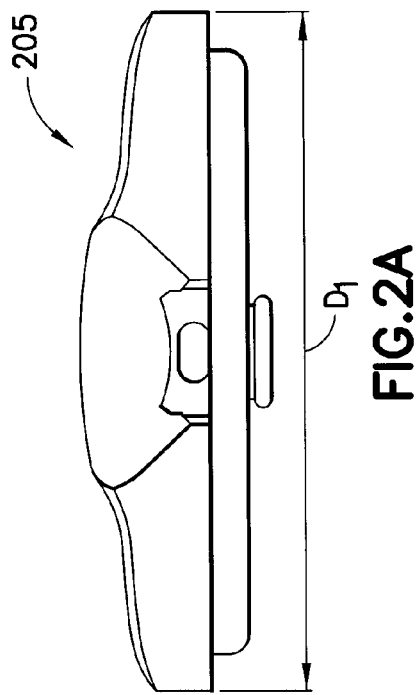
FIGS. 2A-2E show diagrams of a tibial insert according to an embodiment of the present invention (FIGS. 2A and 2B show $D_1$ and $D_2$, used in this context for the purposes of defining the term "size" and FIGS. 2C-2E show axis X, axis Y and axis Z used in this context for the purposes of illustrating each rotational axis).
Figure 2B:
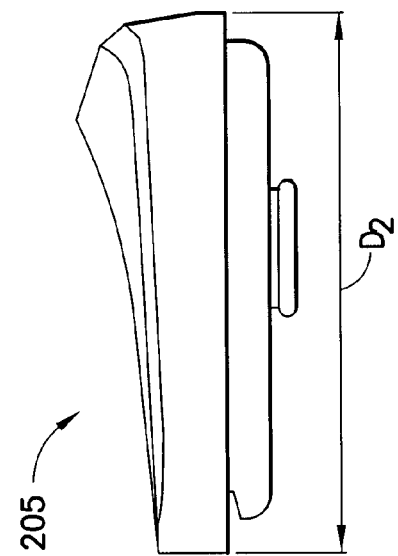
Figure 1:
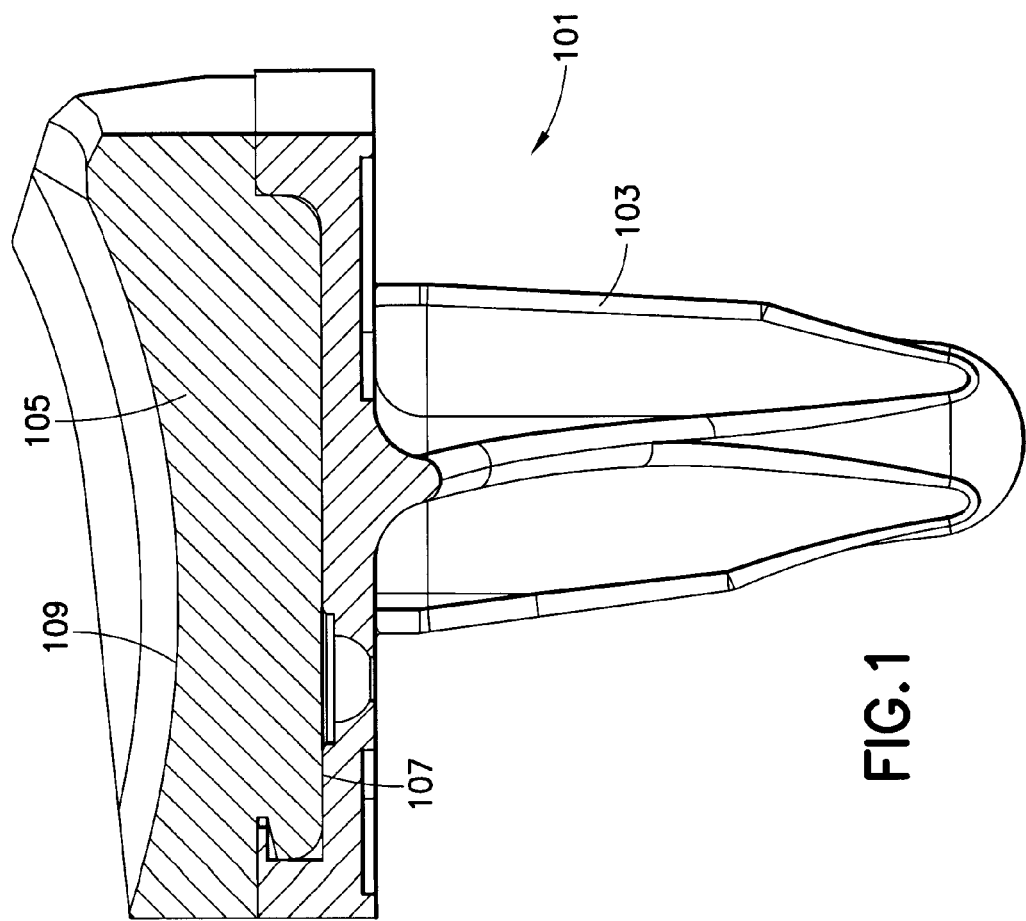
FIG. 1 shows sagittal cross-sectional view of a tibial portion 101 of a total knee arthroplasty ("TKA") prosthesis according to one embodiment of the present invention.
Figure 2C:
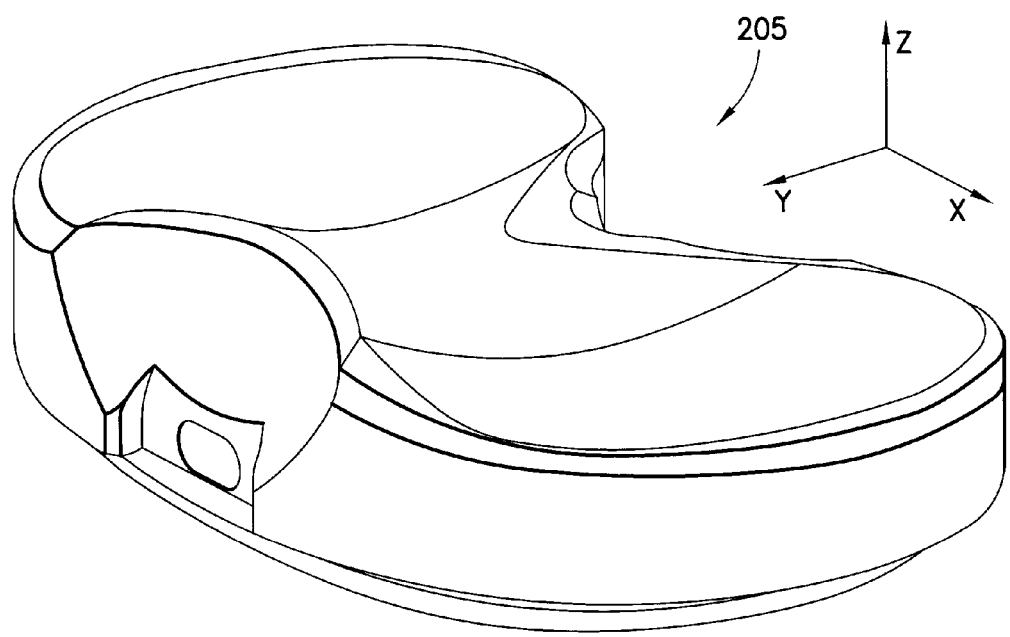
Figure 2D:
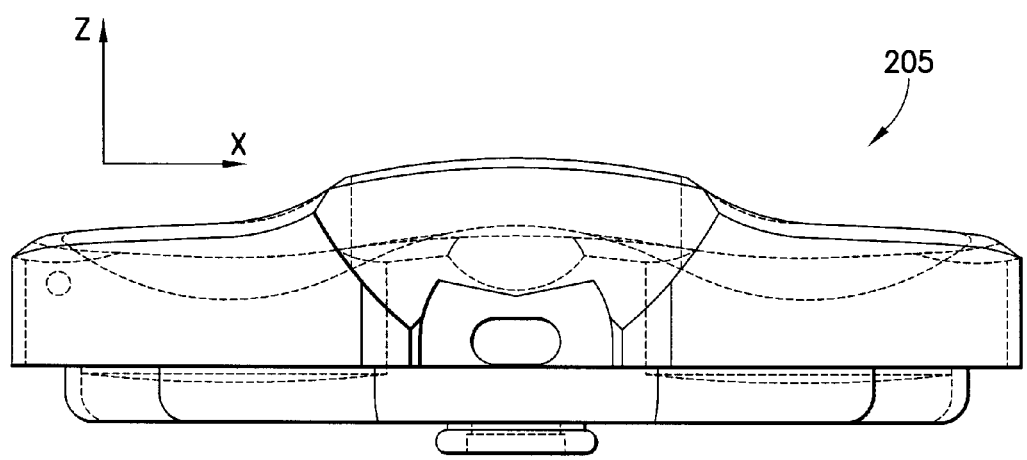
Figure 2E:
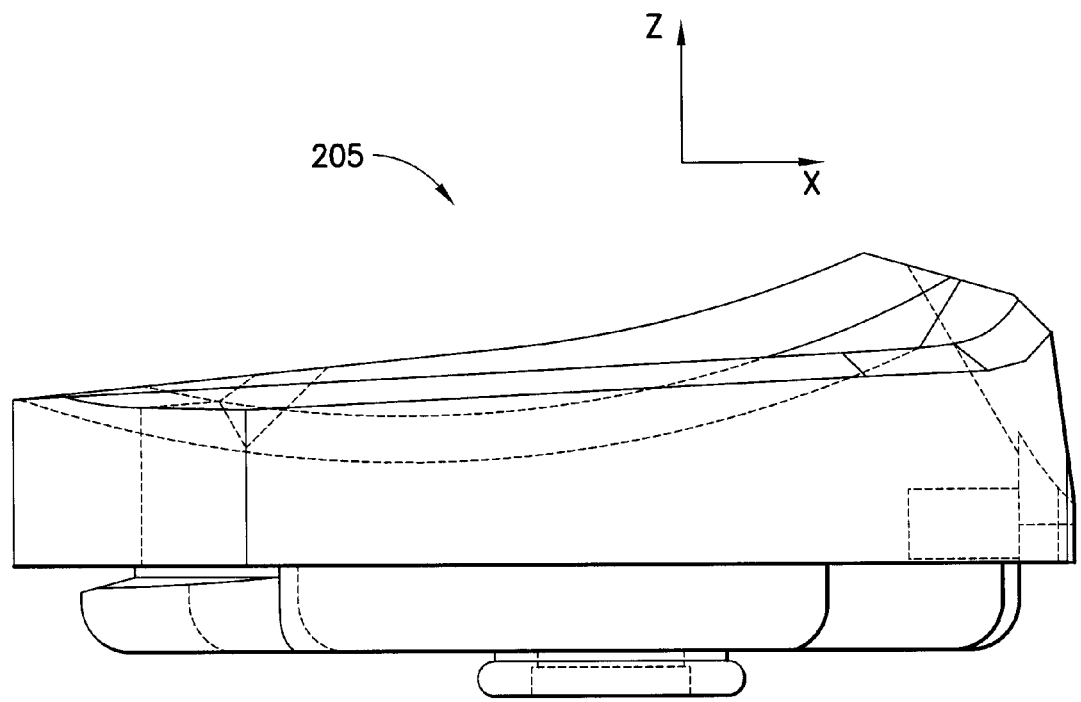
Figure 3:
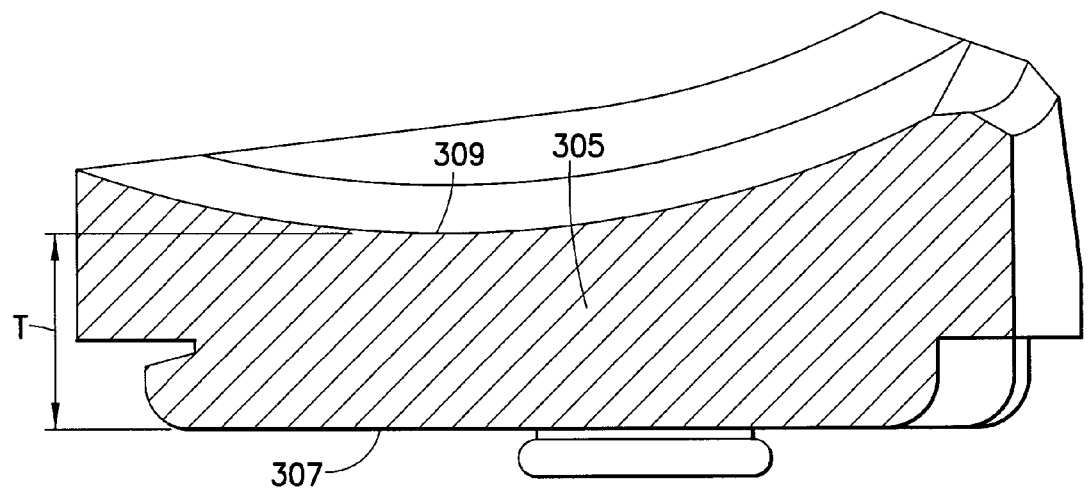
FIG. 3 shows sagittal cross-sectional view of a tibial insert 305 according to an embodiment of the present invention (this FIG. 3 shows distance T, used in this context for the purposes of defining the term "thickness").
Figure 4:
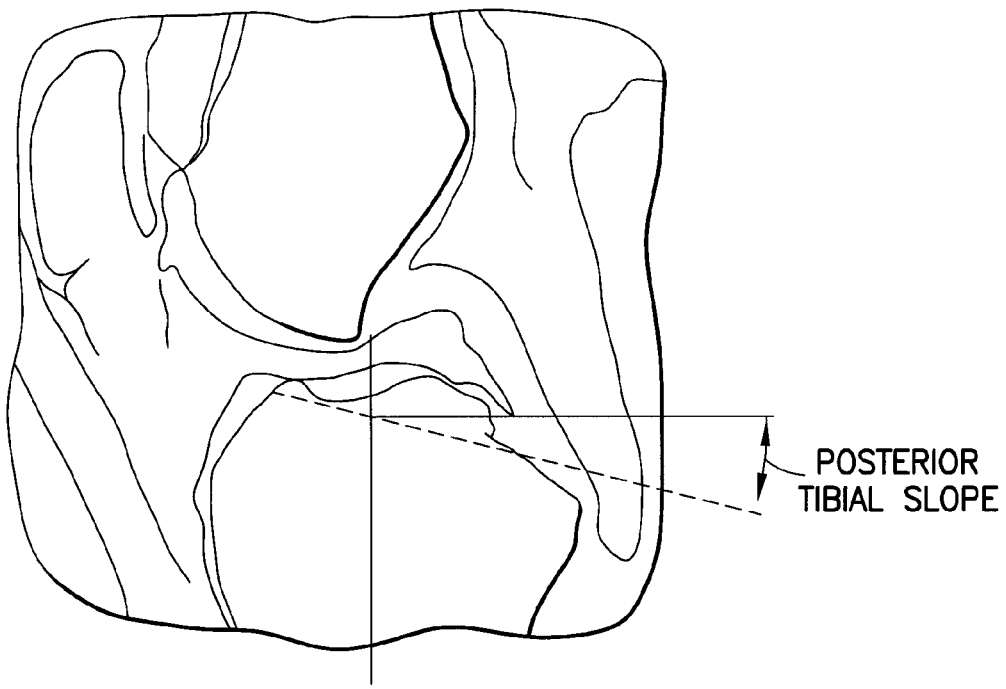
FIG. 4 shows a diagram related to posterior tibial slope.

Among those benefits and improvements that have been disclosed, other objects and advantages of this invention will become apparent from the following description taken in conjunction with the accompanying figures. The figures constitute a part of this specification and include illustrative embodiments of the present invention and illustrate various objects and features thereof. Further, the same reference numerals represent similar elements in the Figures.

DETAILED DESCRIPTION OF THE INVENTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, any figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

As mentioned above, adjusting the posterior tibial slope is conventionally difficult to achieve during surgery. In this regard, various embodiments of the present invention may provide a "family" (that is a plurality) of tibial inserts and/or tibial insert trials with different slopes built-in.

Figure 7:
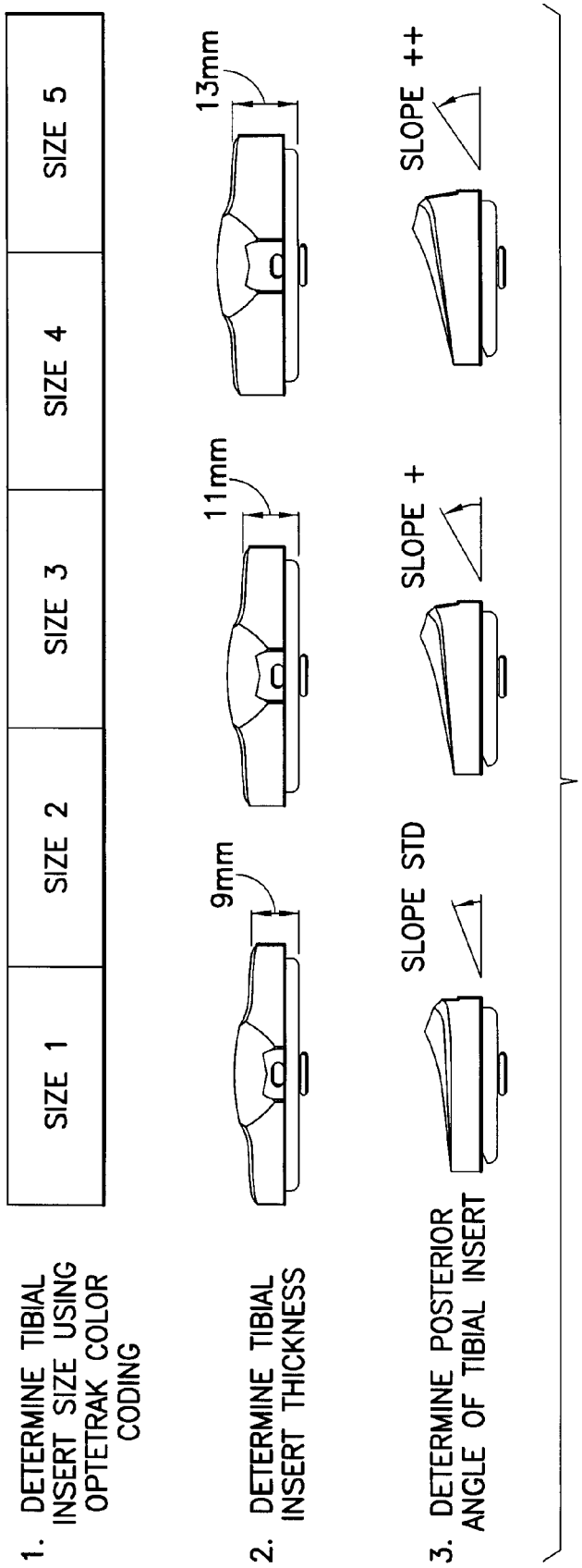
FIG. 7 shows a diagram related an example of defining the optimal tibial insert in three steps according to an embodiment of the present invention.

In use, the surgeon may make the proximal tibial cut (e.g., at a low angle to preserve the PCL) and adjust the posterior tibial slope by determining which sloped tibial insert (and./or tibial insert trial)—from the "family" of tibial inserts (and/or tibial insert trials)—produces optimal results. In this regard, see, FIG. 7, showing an example of defining the optimal tibial insert in three steps: (1) the surgeon determines the proper tibial insert (and/or tibial insert trial) size (in one example, the tibial inserts (and/or tibial insert trials) may be color coded by size; in one more specific example, the tibial inserts (and/or tibial insert trials) may be color coded by size using the EXACTECH OPTETRAK color coding); (2) the surgeon determines the proper tibial insert (and/or tibial insert trial) thickness; and (3) the surgeon determines the proper posterior angle of the tibial insert (and/or tibial insert trial). Of, course, the various sizes, thicknesses, and slopes shown in this FIG. 7 are provided as examples only and are not intended to be restrictive.

After the tibial insert with the optimal built-in posterior tibial slope is implanted, the surgeon has effectively achieved such optimal slope without the need to make additional cuts to the bone.

Figure 8B:
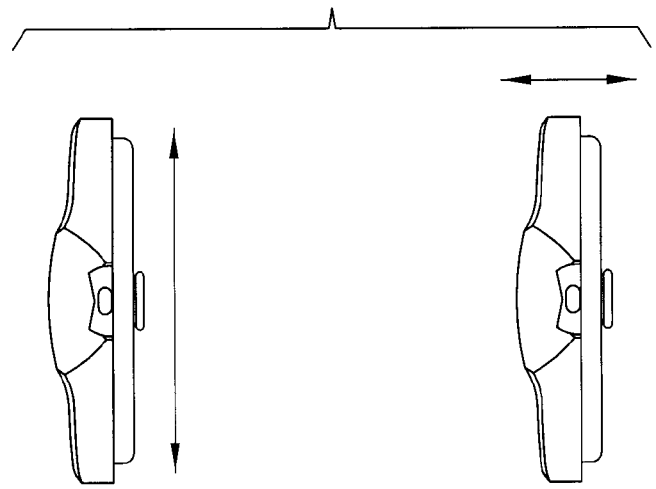
FIG. 8A is a diagram related to showing the choice of 3 parameters (i.e., (1) size; (2) thickness; and (2) posterior slope) that are available to the surgeon to define the optimal tibial insert according to an embodiment of the present invention and 8B is a diagram related to showing the choice of 2 parameters (i.e., (1) size; and (2) thickness) that have conventionally been available to the surgeon.
Figure 8A:
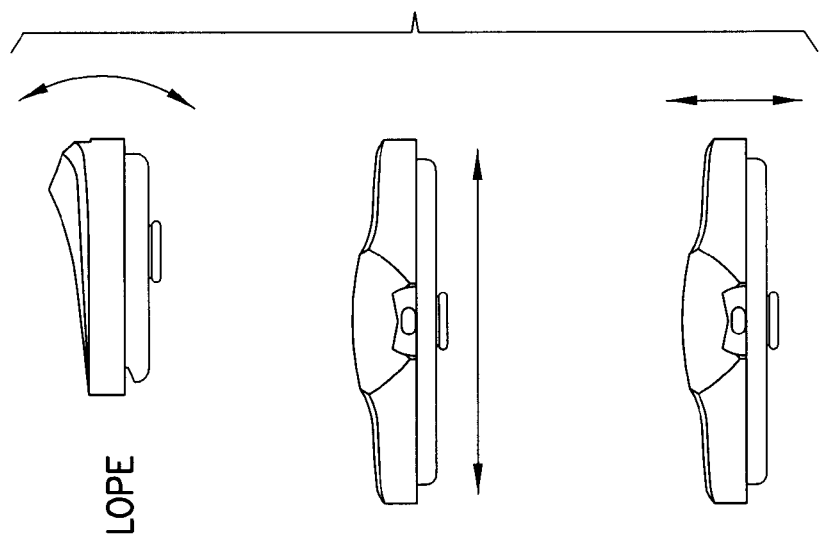

Referring now to FIG. 8A, another illustration showing the choice of 3 parameters discussed above (i.e., (1) size; (2) thickness; and (3) posterior slope) that are available to the surgeon to define the optimal tibial insert (and/or tibial insert trial) according to an embodiment of the present invention are shown (FIG. 8B is an illustration showing a conventional system in which a choice of only 2 parameters (i.e., size and thickness) are available to the surgeon.

Reference will now be made to FIGS. 9-11. Of note, for comparison purposes, three different example slopes (standard, + and ++) are shown in these FIGS. 9-11. Of, course, the slopes shown in these FIGS. 9-11 are provided as examples only and are not intended to be restrictive (e.g., any desired number of positive slopes (relative to "standard") and/or negative slopes (relative to "standard") may be used in connection with various embodiments of the present invention).

FIG. 9A shows how various embodiments of the present invention may help surgeons correctly balance the PCL during total knee arthroplasty by offering a selection of sloped tibial inserts.

Figure 9B:
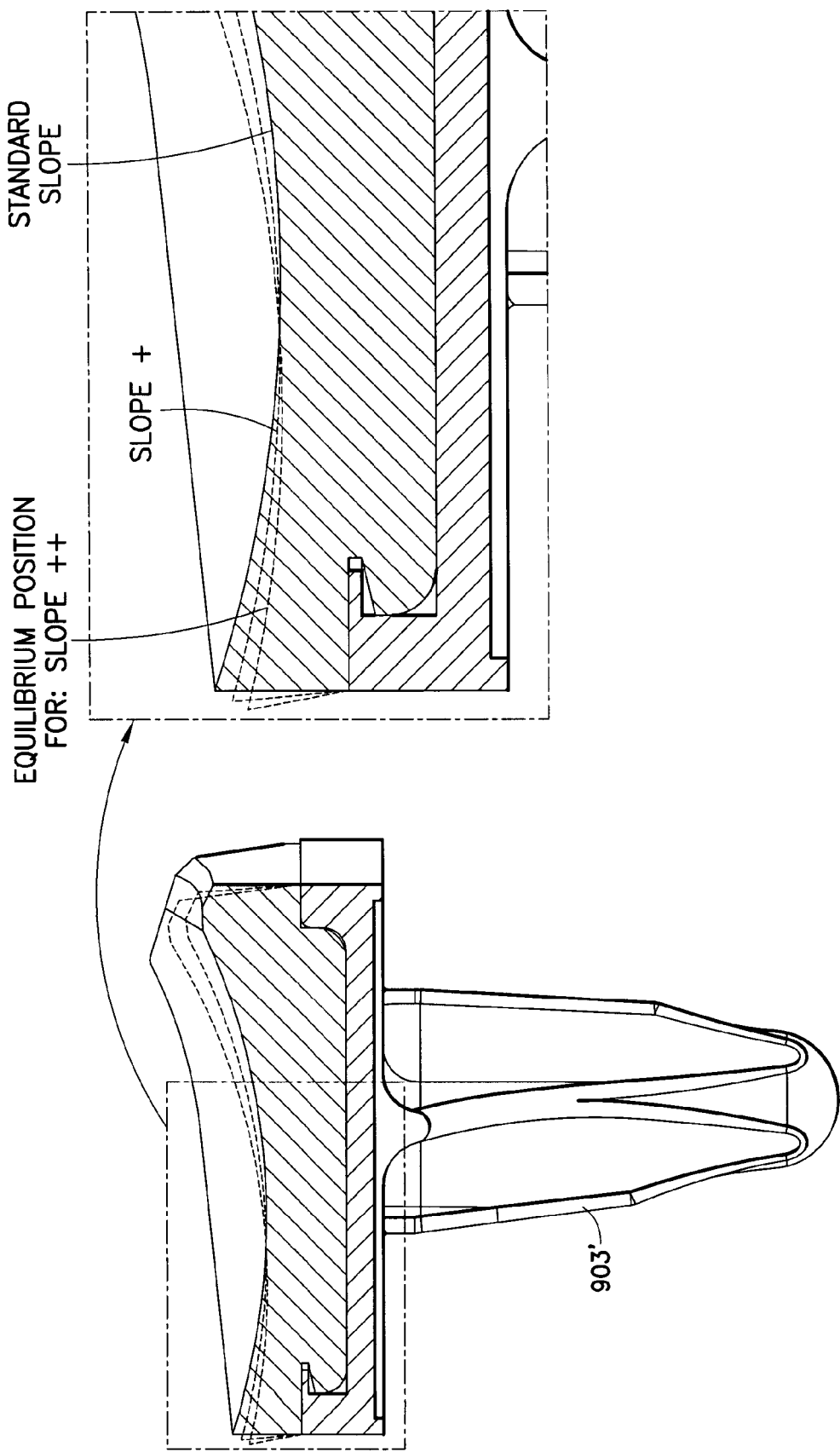
FIG. 9B shows an embodiment of the present invention in sagittal cross-section (the box in the right-hand side of the FIG. shows additional detail regarding equilibrium position for each of three example tibial insert slopes—location of the equilibrium position can fluctuate with the modification of the posterior tibial slope angle). Of course, tibial tray 903' is also shown in this view)

FIG. 9B shows how location (under various embodiments of the present invention) of the equilibrium position may fluctuate with the modification of the posterior tibial slope angle and that managing the correct equilibrium position could also be an important consideration.

FIG. 10 shows how under various embodiments of the present invention: (a) each radius of curvature in the sagittal plane (e.g., of the tibial articulation surface of two or more tibial inserts (or tibial insert trials)—each having a different slope—may be the same; and/or (b) each minimum thickness (i.e., $G_E$ in this FIG. 10) of two or more tibial inserts (or tibial insert trials)—each having a different slope—may be the same.

In one example, only the posterior slope fluctuates from one tibial insert (or tibial insert trial) to the other.

In another example, there may be a vertical delta (i.e., difference) between (or among) two or more tibial inserts (or tibial insert trials)—see, e.g., $G_F$ in this FIG. 10.

Figure 5:
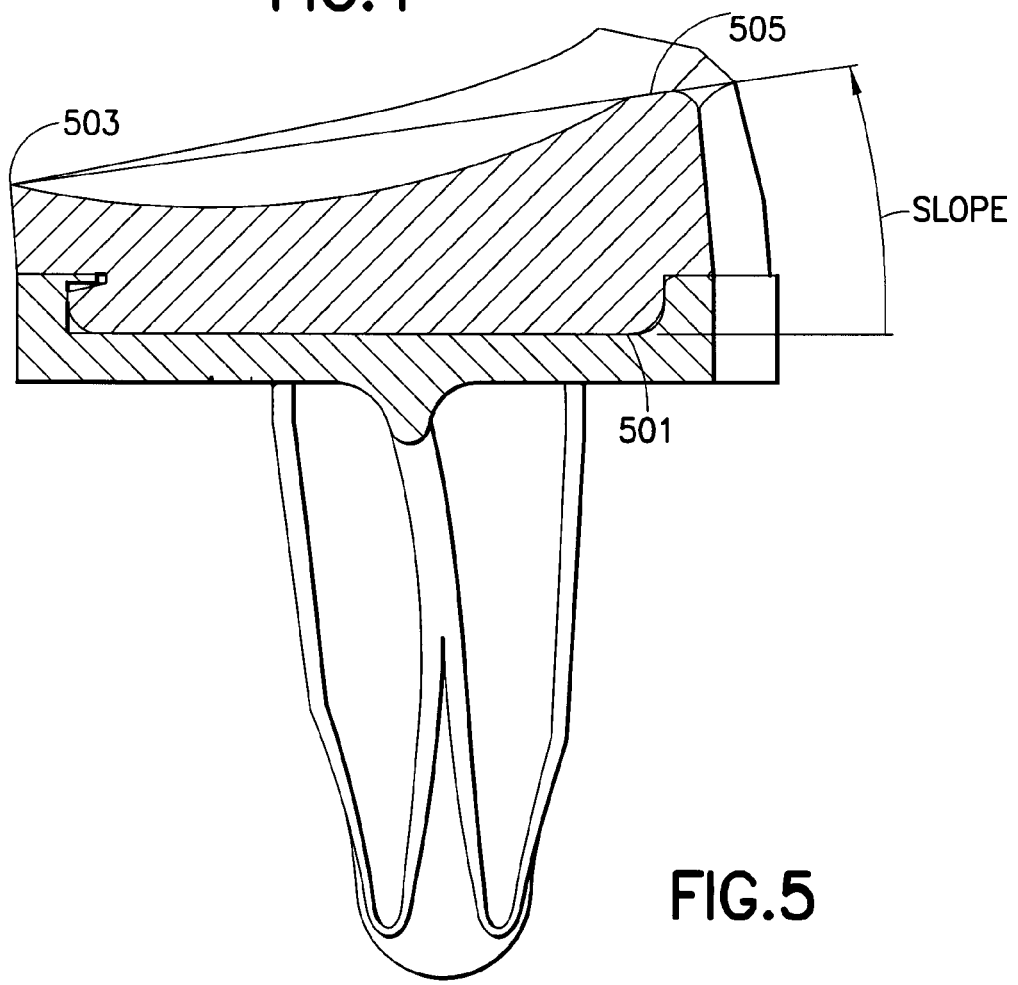
FIG. 5 shows a diagram related to defining the term "slope" for a tibial insert or tibial insert trial for the purposes of describing and claiming the present invention.
Figure 6:
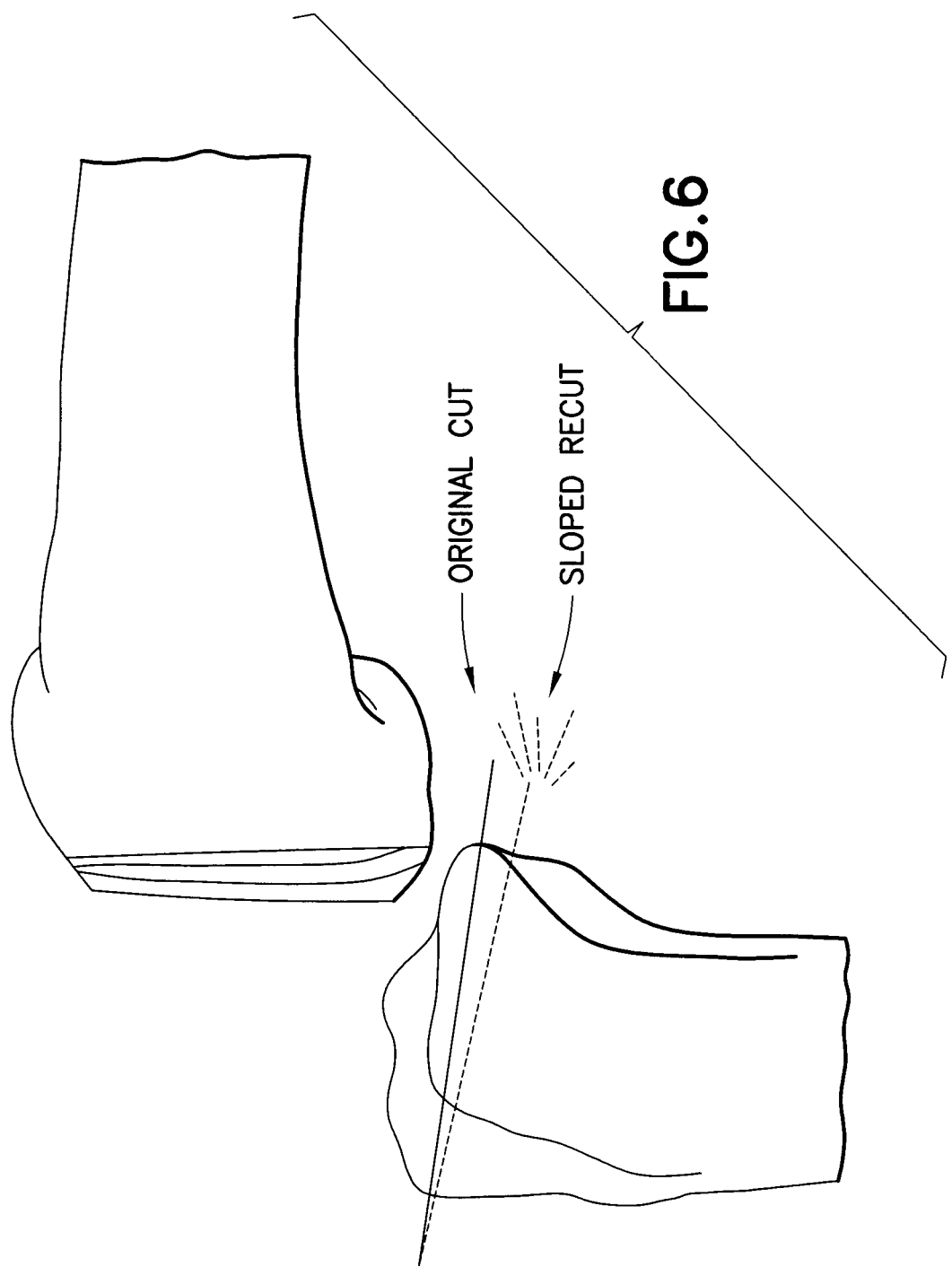
FIG. 6 shows a diagram related to re-cutting the proximal tibia.
Figure 11D:
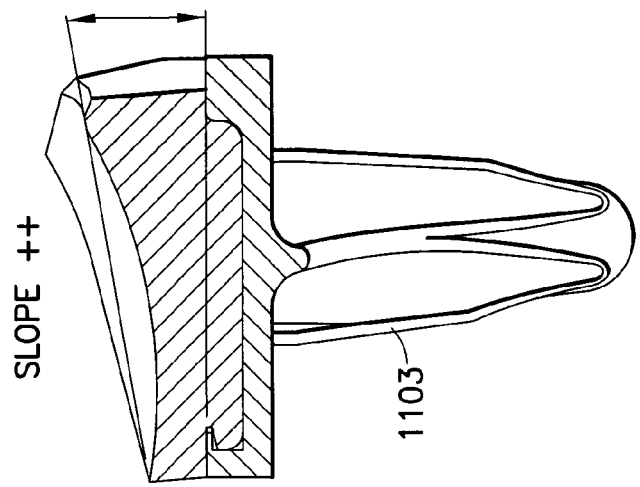
Figure 11C:
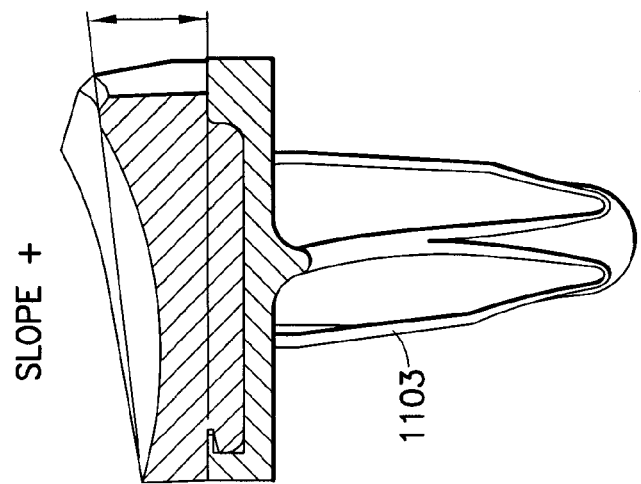
Figure 11B:
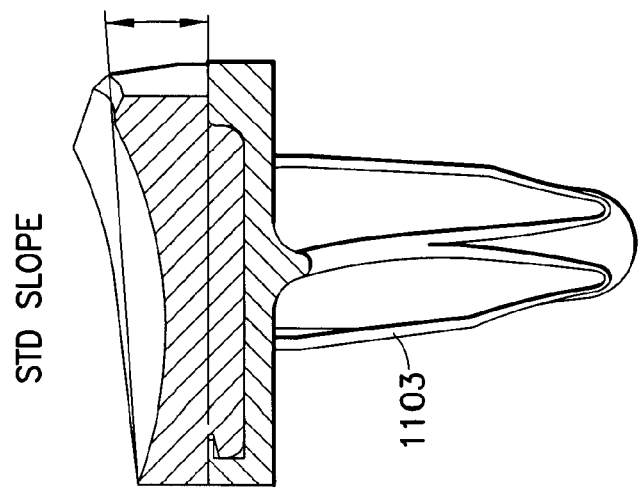

FIGS. 11A-11D show additional detail regarding three different example slopes (tibial tray 1103 is shown in these Figs)—of note, these three example slopes are provided as illustrative illustrations and, of course, are not intended to be restrictive). More particularly, FIG. 11A shows three tibial articular surfaces 1100A, 1100B 1100C (overlaid adjacent another) according to an embodiment of the present invention. FIGS. 11B-11D illustrate the three different slopes of FIG. 11A in a manner similar to the definition of "slope" shown in FIG. 5 (FIG. 11B shows a "standard" slope corresponding to tibial articular surface 1100A of FIG. 11A, FIG. 11C shows a "+" slope corresponding to tibial articular surface 1100B of FIG. 11A and FIG. 11D shows a "++" slope corresponding to tibial articular surface 1100C of FIG. 11A).

As described herein, one embodiment of the present invention is a system, including tibial inserts and tibial insert trials compatible with other femoral and tibial total knee replacement implant components, that effectively address proper tensioning of the PCL. Various embodiments of the present invention may enable surgeons to plan and perform CR total knee arthroplasty around the anatomical and biomechanical preservation of the PCL.

In order to achieve a well-balanced PCL, various embodiments of the present invention provide tibial inserts (and/or tibial insert trials) made from any biocompatible material, available with varying posterior tibial slopes—in addition to choices in size and thickness. By choosing a tibial insert (and/or tibial insert trial) with added or decreased posterior tibial slope, surgeons may fine-tune knee kinematics/ROM at the end of a procedure without additional time-consuming cuts that may result in structural compromise.

Various embodiments of the present invention may include an instrument set with trial tibial inserts having an adjustable posterior slope, or a plurality of trial tibial inserts with various fixed slopes, to be used for determining the optimal posterior slope of the implanted tibial insert, and a selection of tibial inserts with different fixed posterior slopes designed to achieve the correct PCL tension determined during the trial reduction, and, as a result, optimal postoperative knee kinematics.

Further, methods according to various embodiments of the present invention could be used for changing the relative angular position of the articulation surface relative to the distal face of the tibial insert, in order to achieve varied tensioning of the PCL and kinematic behavior.

In one example, during trial reduction, the surgeon may first assemble a trial tibial insert with the standard posterior tibial slope to the trial tibial baseplate. From his evaluation of the PCL tension, the surgeon can open the flexion gap of the knee joint without the need to resect additional tibia by exchanging the standard-slope trial tibial insert with a trial tibial insert having the same size and thickness but also an added posterior tibial slope. This reduces the knee joint space in flexion and decreases PCL tension if needed. Similarly, the surgeon can close the flexion gap of the knee joint by exchanging the standard-slope trial tibial insert with a trial tibial insert of the same size and thickness but also a decreased posterior tibial slope.

According to one example, the system may provide the same number of trial tibial inserts as final implant tibial inserts. For example (which example is intended to be illustrative and not restrictive), the system may include 100 trial tibial inserts: five sizes (1 to 5), four thicknesses (9 mm to 15 mm in 2 mm increments) and five posterior tibial slopes (e.g., slope --, slope -, standard slope, slope +, and slope ++). The surgeon may select the appropriate trial tibial insert based on the assessment of the size, thickness and posterior tibial slope. The surgeon may implant the final tibial insert with the same characteristics as the previously selected trial tibial insert.

Referring now to FIG. 12A, it is noted once again that conventional total knee replacement systems typically utilize tibial inserts that vary according to two parameters: size and the thickness. In contrast, various embodiments of the present invention provide for an optimum reproduction of knee joint kinematics by adding a third parameter: posterior tibial slope (see FIG. 12B).

Figure 13:
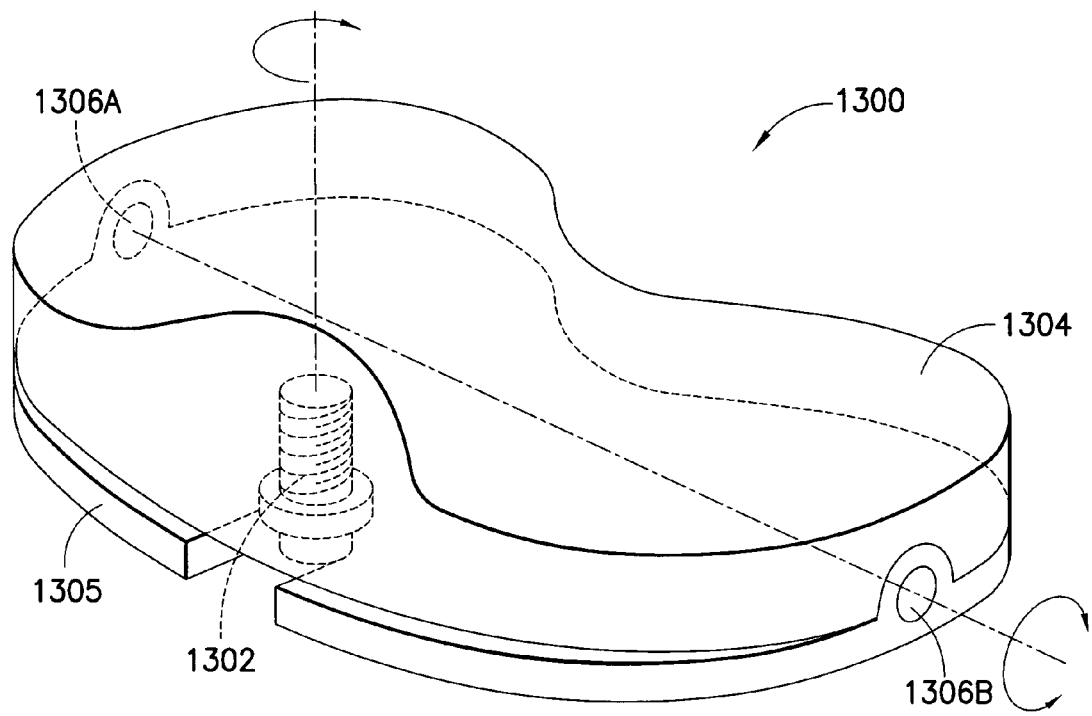
FIGS. 13, 14 and 15 show another embodiment of the present invention related to an adjustable tibial trial insert (FIG. 13 is a perspective view (in partial phantom)
Figure 14:
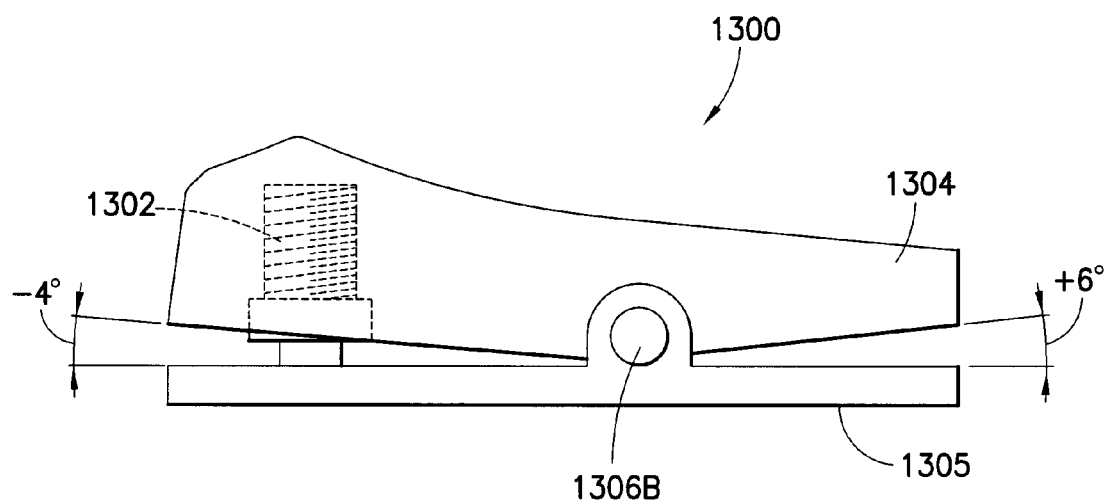
Figure 15:
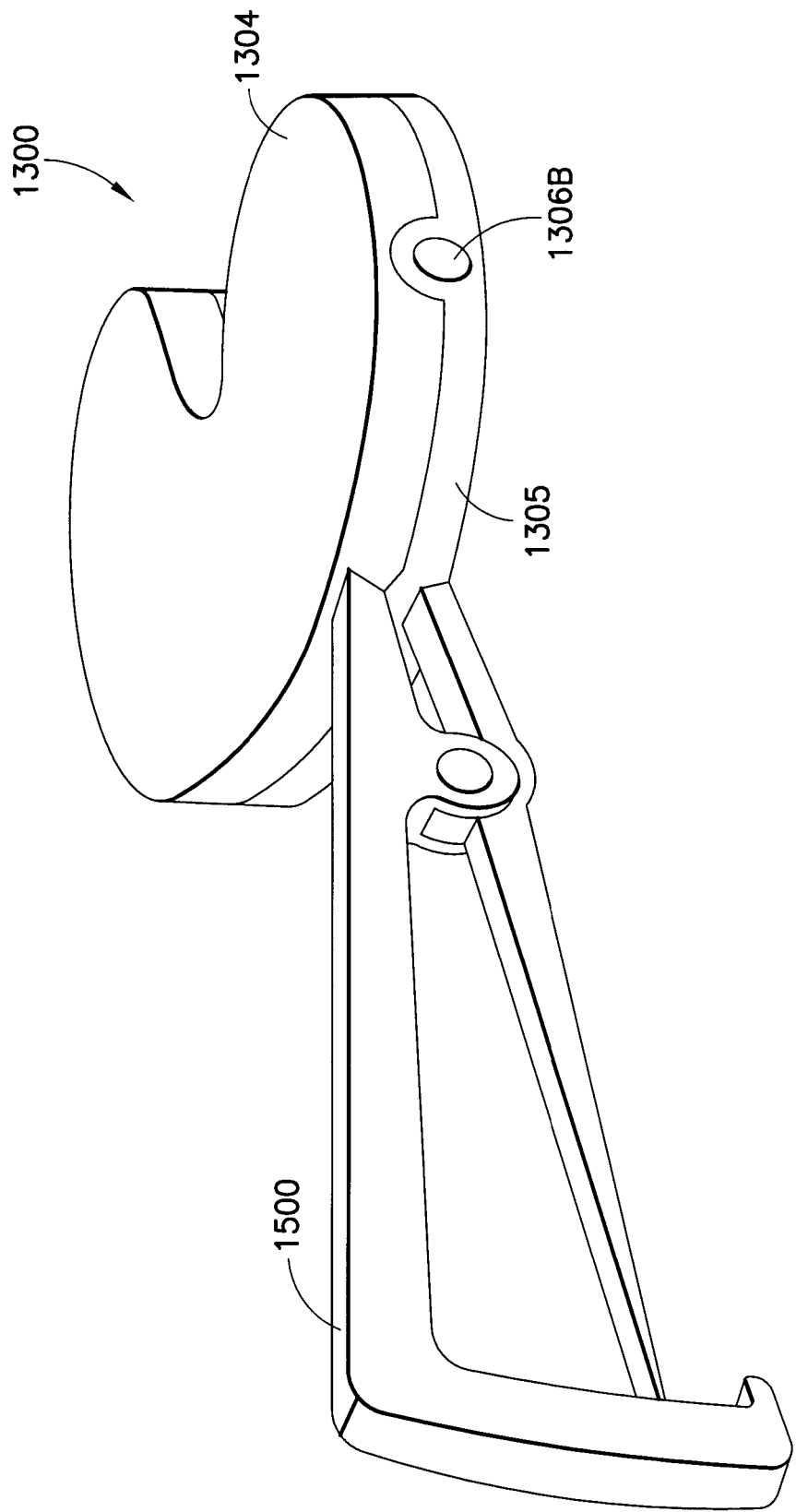

Reference will now be made to FIGS. 13, 14 and 15.

As seen in these FIGS. 13, 14 and 15, another embodiment of the present invention may provide an adjustable tibial trial insert 1300. In one example, the adjustable tibial trial insert 1300 may allow for an adjustment of slope (e.g., the posterior tibial slope parameter). This type of adjustable tibial trial insert 1300 may allow for a significant reduction in the number of trial tibial inserts necessary at the time of surgery (which may, for example, have a positive effect on manufacturing costs and overall instrumentation weight). In addition, if the adjustment of the posterior tibial slope is done with an adjustable trial tibial insert in place, there is no longer the need for, potentially, several trial exchanges (e.g., to define the optimal tension of the PCL).

According to one example, the posterior tibial slope of the adjustable trial tibial insert 1300 may be adjusted by an anterior screw 1302, which allows the body portion 1304 (including the femoral articular surface) to rotate relative to the tibial plate 1305 from, for example, −4° (decreasing the posterior tibial slope) to, for example, +6° (increasing the posterior tibial slope).

In another example, the body portion 1304 may pivot relative to the tibial plate 1305 via pivot pins 1306A,1306B.

In another example, if the gap is bigger than, e.g., 9 mm, the surgeon may attach a 2 mm, 4 mm, or 6 mm spacer to create, respectively, an 11 mm, 13 mm, or 15 mm a tibial trial insert component.

The increase or decrease of the posterior tibial slope offered by the adjustable trial tibial insert may be used as a correction of the tibial cut previously performed by the surgeon. For example, if the surgeon performed a tibial cut according to a posterior slope of 3° (a common posterior slope value), he can correct this angle from, for example, −1° (i.e., +3°−4°) to, for example, +9° (i.e., +3°+6°). The additional angle determined by the adjustable trial tibial insert is, in this example, the correction angle needed to obtain optimal kinematics.

In another example, the correction angle (i.e., the angle between the resected tibia and the corrected proximal surface of the tibial insert) may be measured by attaching a goniometer 1500 (see, FIG. 15) to, for example, the anterior face of the adjustable trial tibial insert (the attachment may be, e.g., via holes provided in the adjustable trial tibial insert).

After reading the corrected posterior tibial slope angle, the surgeon may select the final tibial insert implant with the closest slope value. Considering the same scope as the one used for an embodiment of the invention discussed above, using the adjustable trial tibial insert the number of trial tibial inserts decreases from one hundred (if using monoblock trial tibial insert) to five (i.e., one adjustable trial tibial insert per size) and four spacers for the thickness adjustment.

According to another embodiment of the present invention a mechanism may be included (e.g., in the posterior portion of the trial tibial insert or adjustable trial tibial insert) to determine PCL tension and as a result provide guidance to the surgeon for selecting the appropriate posterior tibial slope.

In another example, various embodiments of the present invention may be utilized in studying the impact of the posterior tibial slope on the function of the PCL.

In another example, various embodiments of the present invention may provide a system comprising a variety of tibial inserts (and/or tibial insert trials) having several posterior slopes in order to achieve an optimum posterior slope while preserving the PCL.

In another example, various embodiments of the present invention may provide an adjustable trial tibial insert (adjustments may include, for example, the posterior slope, axial rotation and/or the AP translation).

In another example, rather than using the adjustable trial tibial insert, a plurality of tibial inserts mimicking the geometry of the adjustable trial tibial insert may be provided.

In another example, a system to evaluate the tension through the trial tibial insert may be provided.

In another example, the tibial insert(s) may be formed partially or fully from ultra high molecular weight polyethylene (UHMWPE).

In another example, the tibial insert trials(s), that is, instruments, may be formed partially or fully from any desired type of copolymer(s) that are easily reprocessed by steam sterilization (e.g., Radel, Ultem, PEEK).

As described herein, various embodiments of the present invention may provide a cruciate-retaining (CR) implant.

In another example, a tibial insert (or tibial insert trial) articular surface may be a tibial condylar articular surface.

In another example, a tibial insert (or tibial insert trial) may have two (or more) condylar articular surfaces.

As described herein, various embodiments of the present invention may provide certain benefits, including (but not limited to):

PCL referencing operative technique:
  Preserve the integrity of the PCL tibial attachment
  Optimal balance of the PCL by the sloped tibial insert
  No need for PCL recession along its tibial attachment
Bone preserving approach:
  Decreased posterior tibial slope of the proximal tibial cut
Straightforward operative technique:
  No need for recut of the proximal tibia to adjust the posterior tibial slope angle As discussed above, both posterior stabilized (PS) and cruciate retaining (CR) total knee replacement systems have demonstrated high rates of survivorship, high clinical knee scores and high patient satisfaction scores over the last few decades. However, CR total knees sometimes exhibit more varied kinematics and a smaller range of motion (ROM) than similar PS knees. One cause of this is a posterior cruciate ligament (PCL) that does not optimally work with the tibial insert, allowing for paradoxical femoral anterior translation in flexion and impingement between the posterior lip of the tibial insert and the posterior femur. This appears to be related to difficulty preserving optimal PCL tension during surgical tibial preparation.

A basic, conventional technique for preparing the proximal tibial bone during total knee surgery calls for the tibial cutting block to be positioned according to several parameters:

Frontal plane alignment
Rotational alignment
Sagittal alignment
Resection depth

Frontal alignment is achieved by aligning the shaft of the tibial resector (which can be intra-medullary or extra-medullary) with the long axis of the tibia. In this case, the proximal tibial cut is performed perpendicular to the tibia long axis.

Rotational alignment is set by aligning the guide with the second toe or, if there is an ankle or foot deformity, by pointing the guide in the same direction that the tibial tubercule points.

Sagittal alignment is achieved by reproducing the posterior slope of the particular tibia.

Figure 17:
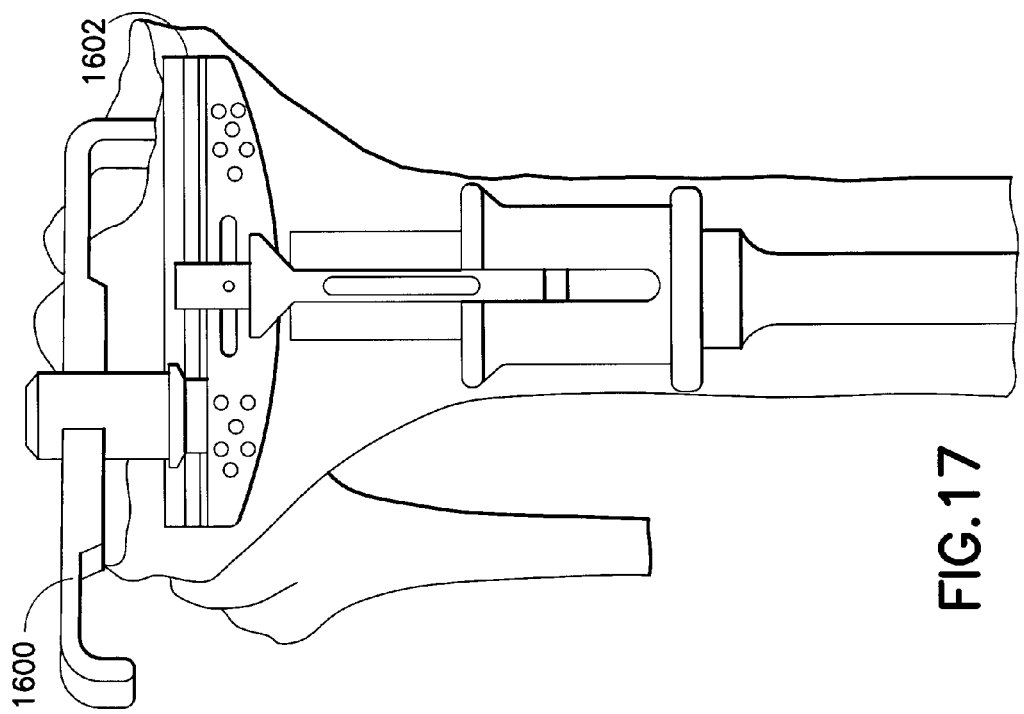
FIGS. 16 and 17 show two uses of a conventional tibial cutting block and depth resection stylus.
Figure 16:
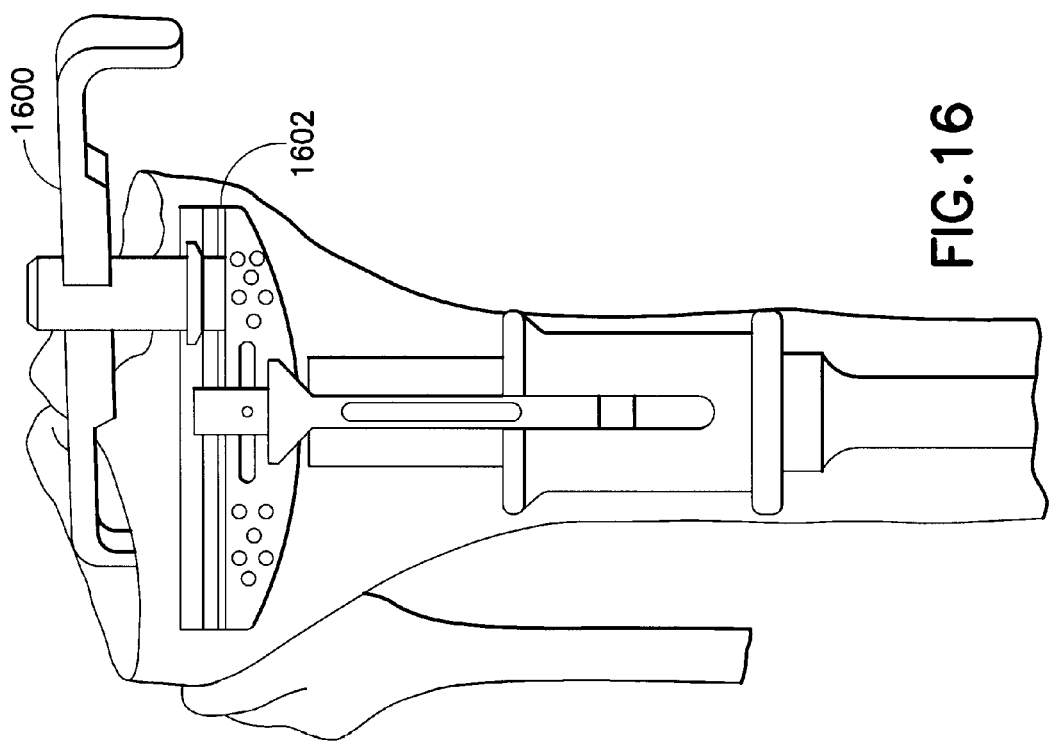

Finally, resection depth is defined by referencing the "most normal" or "most defective" tibial plateau (see FIGS. 16 and 17—FIG. 16 shows that according to a conventional method, the depth resection stylus 1600 is placed in the cutting slot of the proximal tibial cutting block 1602 and the end of the stylus marked "most normal" is placed on the center of the most normal tibial plateau. This level resects 10 mm of bone; FIG. 17 shows, alternatively, the depth resection stylus 1600 is placed in the cutting slot of the proximal tibial cutting block 1602 and the end of the stylus marked "most defective" is placed on the center of the most defective tibial plateau. This level of bone resection is 1 mm below the plateau where the stylus rests.

In CR component implantation, this tibial preparation may compromise PCL integrity and tension and, as a result, postoperative function.

Figure 18:
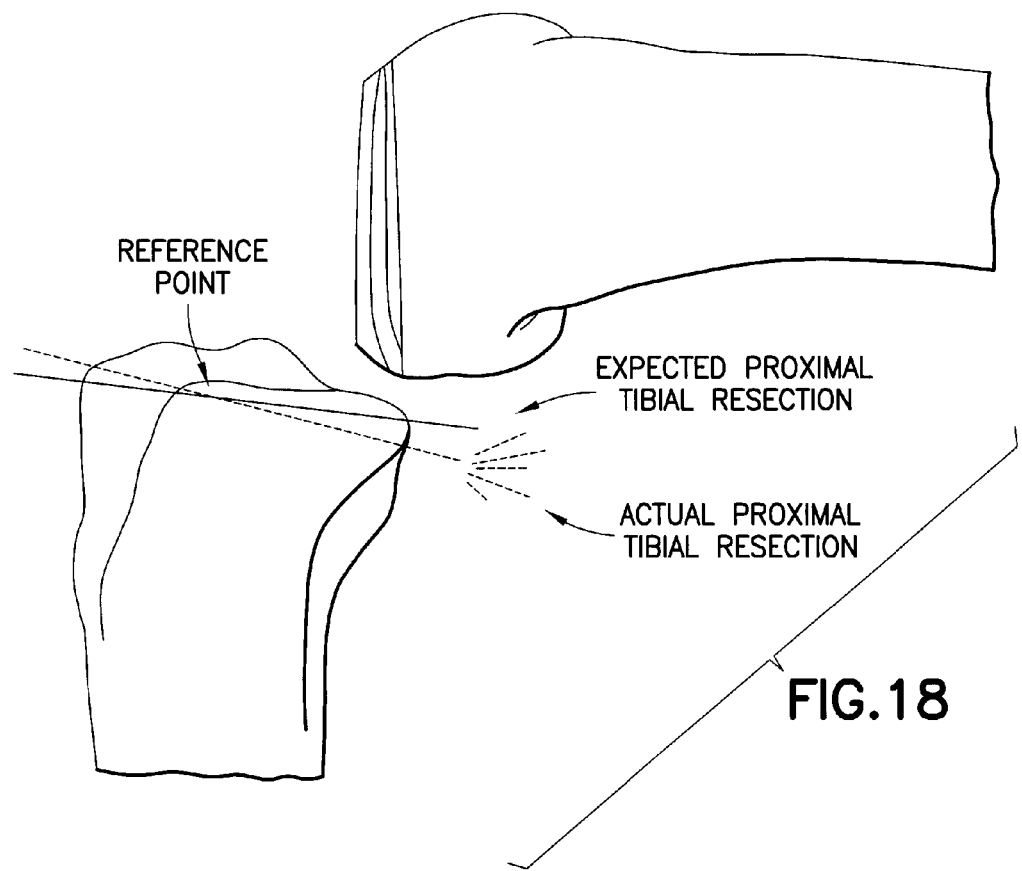
FIG. 18 shows that, typically, due to the absence of a landmark for sagittal alignment, proximal tibial resection slope may be greater than intended, damaging the PCL tibial attachment.

First of all, reproducing the posterior slope of a particular tibia is typically difficult due to the lack of a landmark (e.g., a landmark for sagittal alignment). As a result, angular tolerance associated with posterior slope reproduction during total knee arthroscopy has been reported to be as much as ±3°. If the angle of proximal tibial resection is greater than expected, the PCL tibial attachment can be damaged, irreversibly sacrificing its function (see FIG. 18).

Secondly, depending on the posterior slope of the proximal tibial resection, orientation of the knee joint line may not be optimum, interfering with PCL function. Because tibial inserts have typically been available with a fixed slope the angle of the proximal tibial resection dictates the orientation of the knee joint line. In order to accommodate PCL tension from this orientation, a number of different surgical techniques have been suggested. These include increasing the slope of the proximal tibial resection, release of the PCL along its tibial attachment, and resection of additional posterior femoral bone. Each of these approaches can have negative consequences for PCL function and CR total knee replacement performance.

From this explanation, it becomes clear that typical tibial preparation is not fully effective for CR total knee replacement, where tension and conservation of the PCL is vitally important.

Therefore, various embodiments of the present invention provide a method (and associated system) for predictably positioning a tibial component based on respect and conservation of the PCL tibial attachment.

One embodiment of the present invention is the referencing of the PCL tibial attachment rather than the tibial plateau for proximal tibial resection. This provides surgeons assurance that the proximal tibial resection will be above the PCL tibial attachment. Such referencing may be achieved through use of a specifically designed PCL stylus pointer and PCL retractor (discussed in more detail below).

Figure 19:
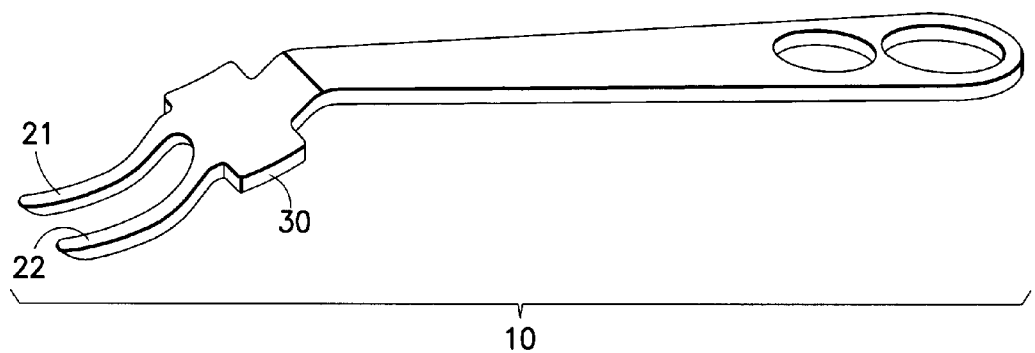
FIG. 19 shows a PCL retractor according to an embodiment of the present invention.

The PCL retractor of this example, a so-called "no-touch" PCL retractor (see FIG. 19), is designed to subluxate the posterior margin of the tibia anterior to the femur. The PCL retractor 10 includes two prongs 21 and 22 (one medial and one lateral to the PCL) intended to contact the posterior margin of the tibia. The spread between the prongs is sufficient to provide clearance on the medial and lateral aspects of the PCL. In the sagittal plane, the prongs feature a curvature intended to provide clearance between the PCL retractor on the anterior portion of the PCL. Also, the PCL retractor 10 includes a large femoral plate 30 intended to protect the femoral distal cut. The special design of this instrument provides an appropriate subluxation while preserving the PCL by essentially eliminating any risk of retractor interference with the PCL.

Figure 20:
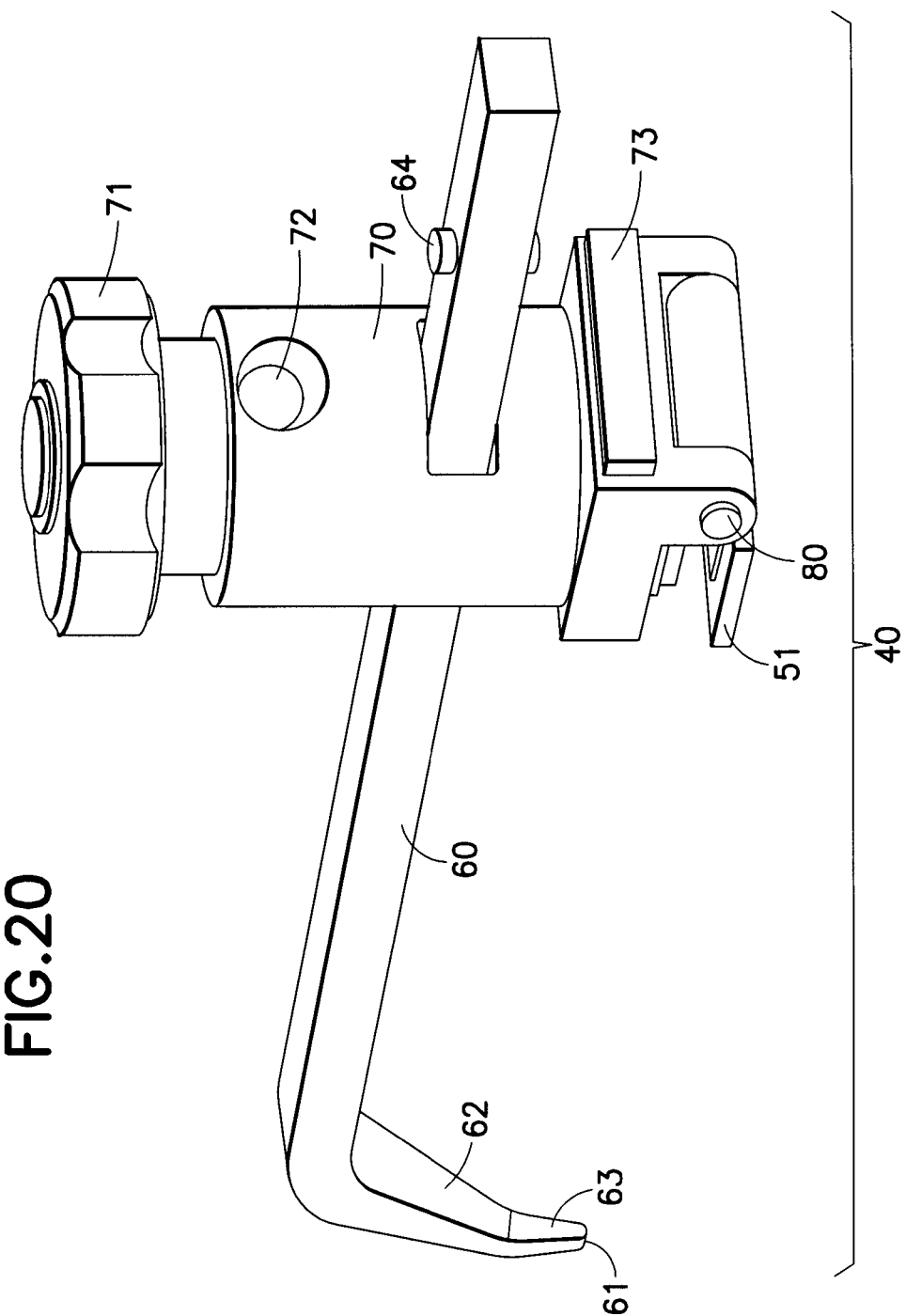
FIG. 20 shows a PCL stylus (and associated instrumentation) according to an embodiment of the present invention.

Referring now to FIG. 20, an example, PCL stylus (and associated instrumentation) is shown (this example PCL stylus (and associated instrumentation) enables PCL tibial attachment referencing).

As seen in this FIG. 20, this instrument is intended to be attached to a standard tibial cutting block (not shown), by introducing the tang 51 of the instrument 40 into the slot of the tibial cutting block (the tang may be, for example, releasably locked into the slot of the tibial cutting block). The slot of the tibial cutting block is intended to receive a sawblade to make the proximal tibial cut. In one example, in order to allow an easy connection and maintain accurate positioning of the instrument 40 relative to the tibial cutting block, the thickness of the tang 51 may be slightly undersized relative to the thickness of the slot. From this setting, the surgeon may place the tip 61 of the stylus 60 in contact with the PCL tibial attachment (not shown). In order to achieve this, the surgeon may utilize several adjustments.

First, the instrument 40 may include a "flip-up" connection—which allows the stylus 60 and body 70 to rotate as an assembly around an axis 80 relative to the tang 51 and then the tibial cutting block (see, e.g., FIGS. 21A and 21B). The release of the "flip-up" connection may be achieved by simply pushing a spring loaded button 73. This adjustment may be useful to allow the tip 61 of the stylus 60 to pass above the tibial eminence (not shown) while the instrument 40 is firmly attached to the tibial cutting block. Once the tip 61 of the stylus 60 is posterior to the tibial eminence, then the surgeon only needs to rotate the stylus 60 back and lock it in place.

Another adjustment available to the surgeon in this example resides in the translation of the stylus 60 relative to the body 70 of the instrument 40 (see, e.g., FIG. 22). This translation allows the adjustment of the stylus 60 depending of the size of the tibia (not shown). The translation of the stylus 60 may be limited by a cross-pin 64 intended to contact the body 70 of the instrument 40 as a stop (the stylus may be, for example, releasably locked to the body with regard to translation of the stylus).

The pointer portion of the stylus 60 may include a special low profile combining an oblique portion 62 and a straight 63 portion. The oblique portion 62 of this example, is intended to avoid impingement with the femur (not shown), while the straight portion 63 of this example allows good probing of the tibial PCL attachment (not shown).

Figure 23A:
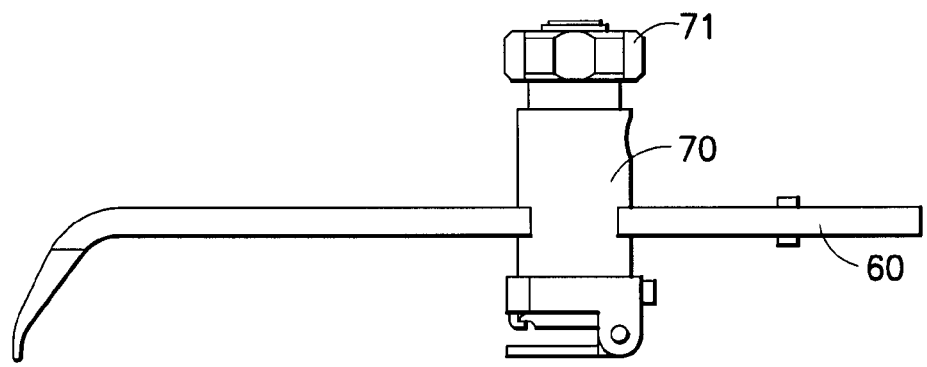
FIGS. 23A-23C and 24A-24C show the PCL stylus (and associated instrumentation) of FIG. 20 (wherein the views of FIGS. 23A and 24A show the stylus at a first height (relative to the mounting element); the views of FIGS. 23B and 24B show the stylus at a second (higher) height (relative to the mounting element); and the views of FIGS. 23C and 24C show the stylus at a third (even higher) height (relative to the mounting element). Of note, the different heights may be seen clearly in these Figs. by reference to the horizontal dashed line of FIGS. 23A-23C.
Figure 23B:
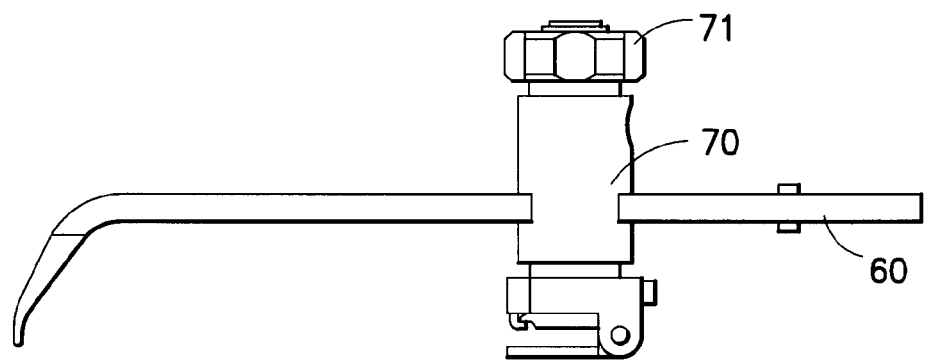
Figure 23C:
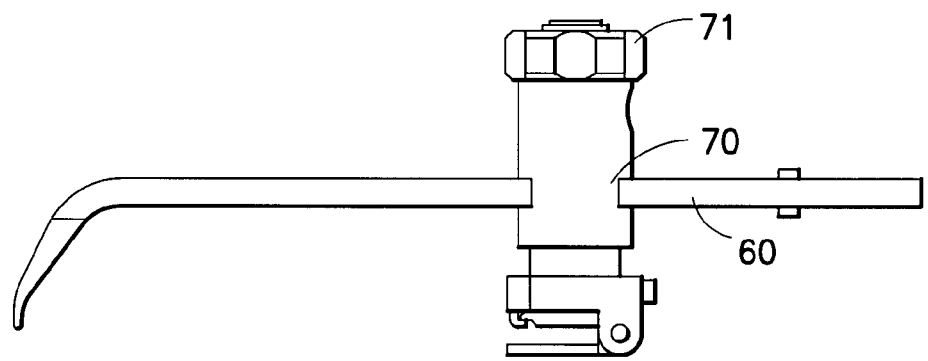

Using these adjustments, the surgeon may place the tip 61 of the stylus 60 as close as possible to the PCL tibial attachment (not shown). It may be case where the PCL tibial attachment is surrounded of fibrous tissue making it difficult to probe. For such case, the instrument 40 may provide for height adjustment (see FIGS. 23A-23AC and 24A-24C). In this example, by turning the knob 71 of the body, the surgeon translates the stylus 60 up and down relative to the tibial cutting block (not shown) and then compensates for the actual position of the tip 61 of the stylus 60 relative to the PCL tibial attachment.

Figure 24A:
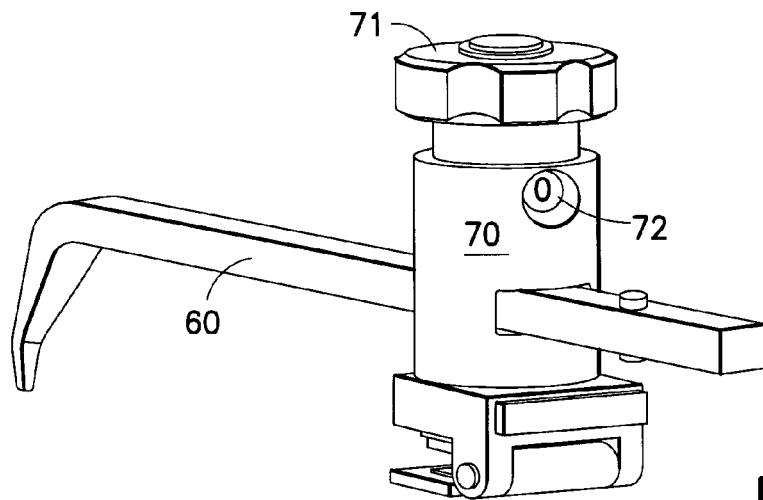
Figure 24B:
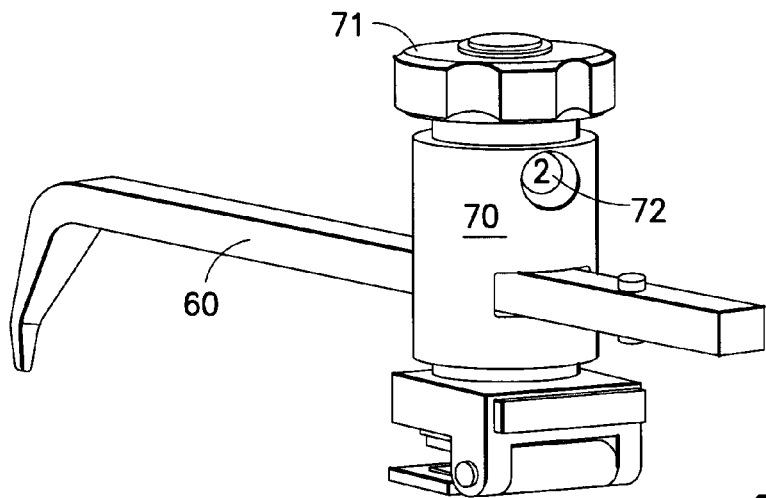
Figure 24C:
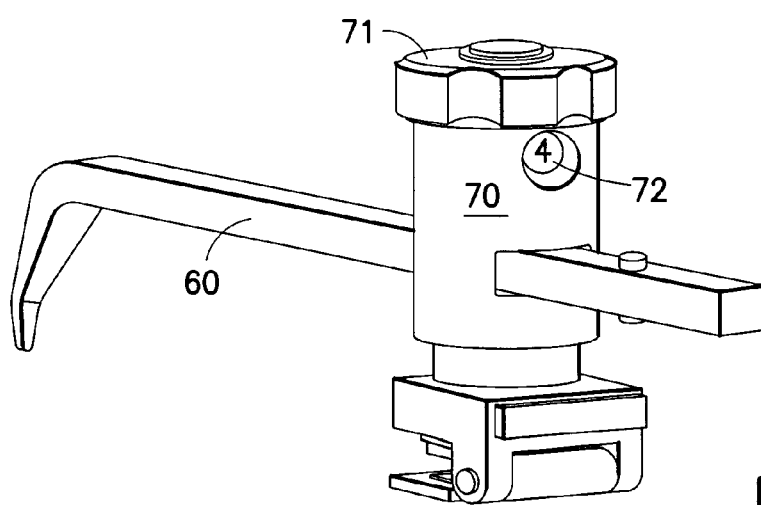

Reference will now be made to an example providing certain details regarding the reading of the vertical translation 72 through a window on the face of the body 70 (see FIGS. 24A-24C).

As seen, when the reading of the vertical translation 72 is equal to "0", the sawblade (not shown) (and then the proximal tibial resection) will be at the same location as the tip 61. A positive value of the vertical translation 72 signifies that the sawblade (not shown) will exit the tibia distally (i.e. below) to the tip 61 of the stylus 60 by the same amount of the reading. From this point, it is well understood that the PCL retractor of this embodiment provides adequate exposure of the PCL tibial attachment, and the PCL stylus references the PCL tibial attachment to ensure proximal tibial resection will be above the PCL tibial attachment.

In another embodiment of the present invention (and as discussed above) a method is provided for correcting the posterior tibial slope after proximal tibial resection, in order to produce an optimum knee joint line. As mentioned previously, the angular tolerance associated with posterior tibial slope is relatively large, which means the proximal tibial resection slope may need to be adjusted to correctly match the appropriate knee joint line. In order to achieve this, tibial inserts (and or trial insert trials) may be provided with different slopes (in addition to different sizes and thicknesses). Using this feature, surgeons can independently modify the slope regardless of the slope of the proximal tibial resection (e.g., within a range of 10 degrees).

As discussed herein, various embodiments of the present invention provide for referencing the PCL tibial attachment as a fixed pivot point using PCL-oriented instruments and restoring the knee joint line by choosing the appropriate slope of the tibial insert to be implanted.

Reference will now be made to FIGS. 25A, 25B, 26A, 26B, 27A and 27B, which represent different scenarios of proximal tibial resection and explain the principle of angular slope correction to produce an appropriate knee joint line.

Figure 25B:
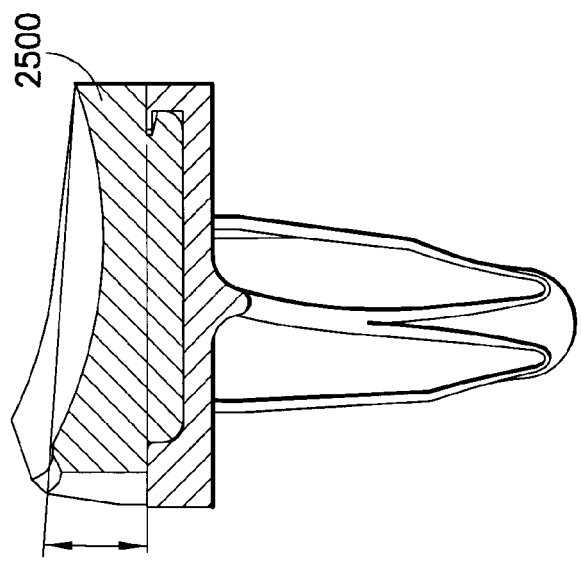
FIG. 25A shows the PCL stylus (and associated instrumentation) of FIG. 20 as applied to a patient's bone and FIG. 25B shows an example low slope tibial insert for use in the example scenario shown in FIG. 25A (that is, the slope of the proximal tibial resection (- - -) is greater than the expected resection (—), so the surgeon will correct it by using a tibial insert featuring a reduced, built-in slope in order to match the orientation of the ideal knee joint line ( . . . )).
Figure 25A:
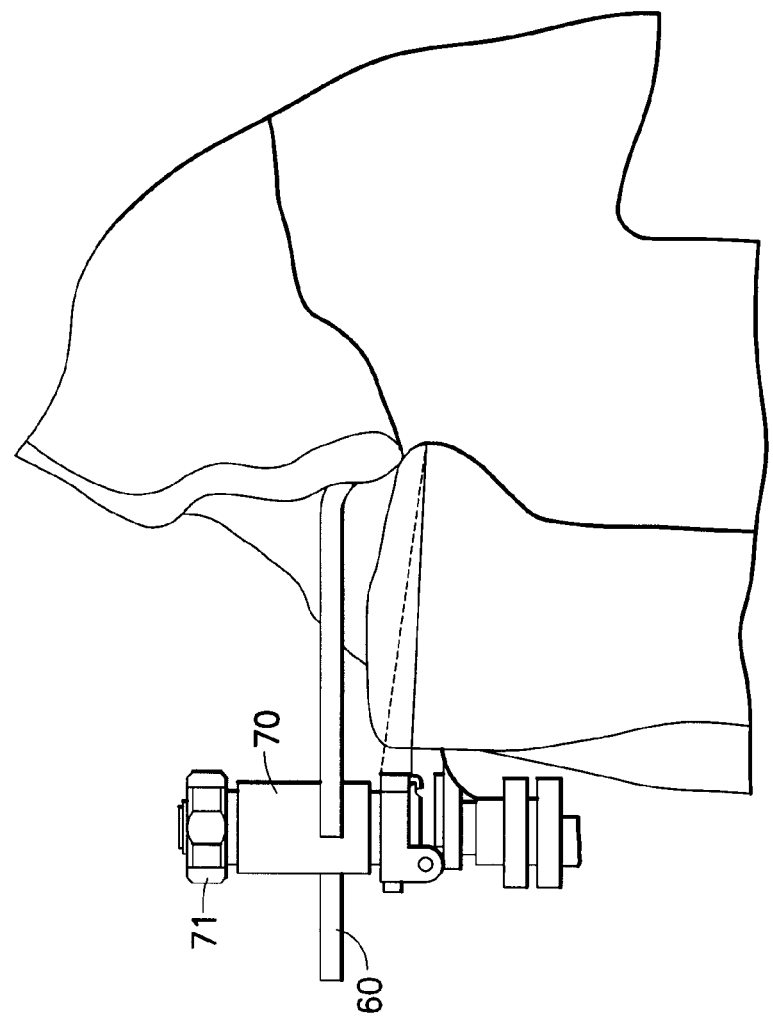

More particularly, as seen in FIGS. 25A and 25B, the slope of the proximal tibial resection (- - -) is greater than the expected resection (—), so the surgeon will correct it by using a tibial insert 2500 having a reduced, built-in slope in order to match the orientation of the ideal knee joint line ( . . . ).

Figure 26B:
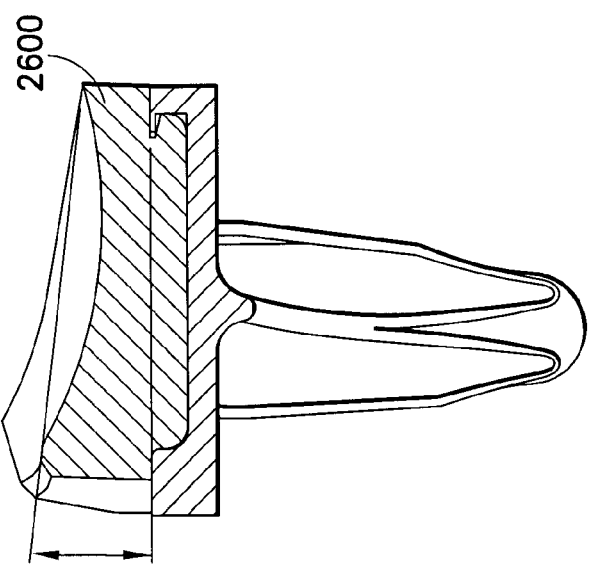
FIG. 26A shows the PCL stylus (and associated instrumentation) of FIG. 20 as applied to a patient's bone and FIG. 26B shows an example neutral slope tibial insert for use in the example scenario shown in FIG. 26A (that is, the slope of the proximal tibial resection (- - -) is as expected, so the surgeon will use a neutral (or standard) tibial insert in order to match the orientation of the ideal knee joint line ( . . . )).
Figure 26A:
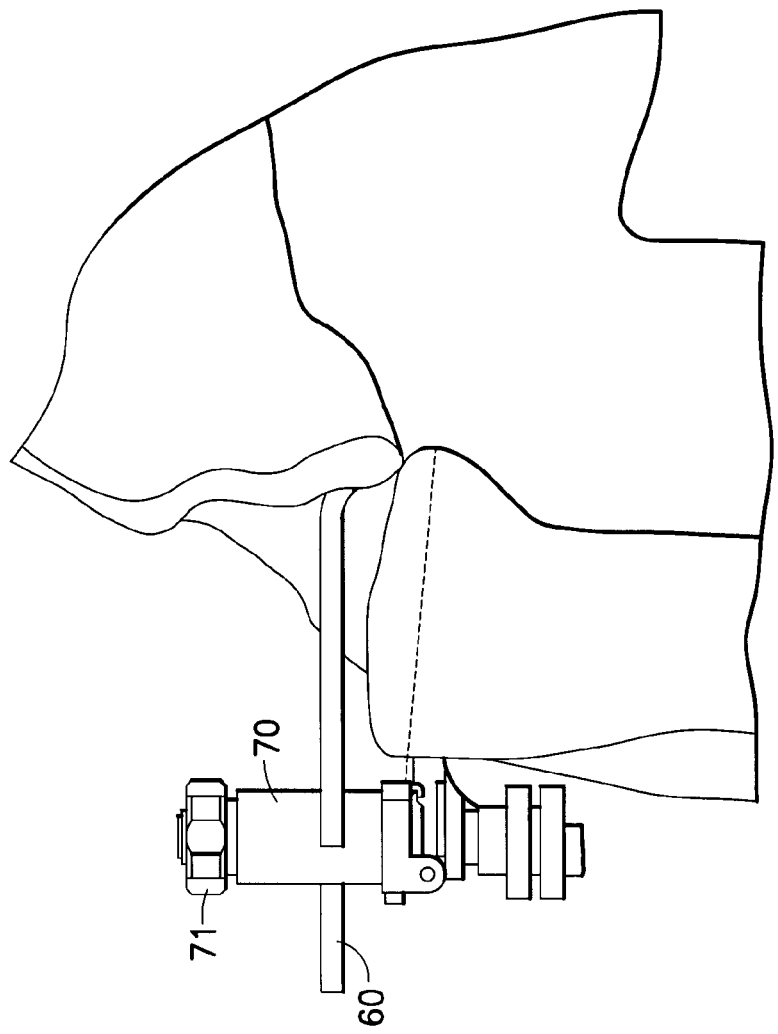

Further, as seen in FIGS. 26A and 26B, the slope of the proximal tibial resection (- - -) is as expected, so the surgeon will use a neutral (or standard) tibial insert 2600 in order to match the orientation of the ideal knee joint line ( . . . ).

Figure 27B:
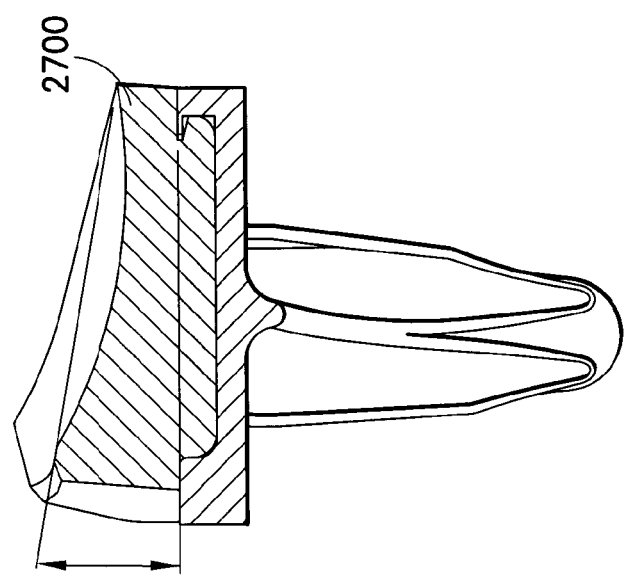
FIG. 27A shows the PCL stylus (and associated instrumentation) of FIG. 20 as applied to a patient's bone and FIG. 27B shows an example low slope tibial insert for use in the example scenario shown in FIG. 25A (that is, the slope of the proximal tibial resection (- - -) is smaller than the expected resection (—), so the surgeon will correct it by using a tibial insert featuring a built-in increased slope in order to match the orientation of the ideal knee joint line ( . . . )).
Figure 27A:
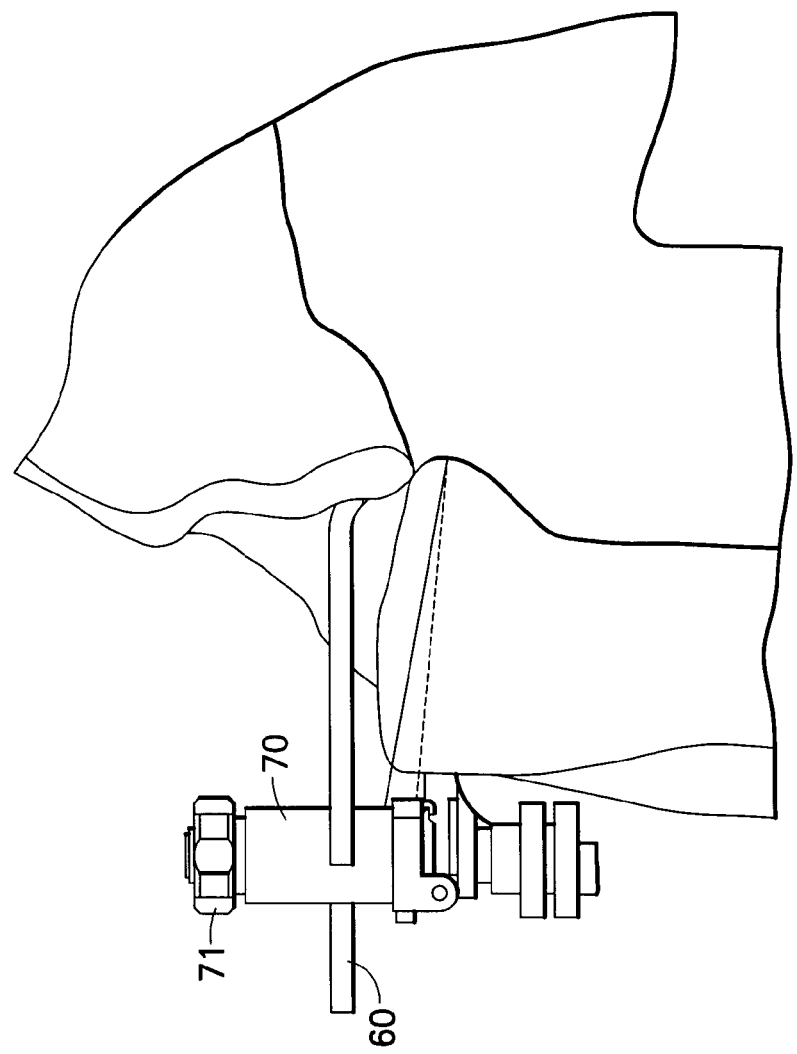

Further, as seen in FIGS. 27A and 27B, the slope of the proximal tibial resection (- - -) is smaller than the expected resection (—), so the surgeon will correct it by using a tibial insert 2700 having a built-in increased slope in order to match the orientation of the ideal knee joint line ( . . . ).

As mentioned, a conventional method of implantation requires different surgical techniques to adjust the PCL to the implanted tibial component; which can have negative consequences for PCL function and/or CR total knee replacement performance in general.

In this regard, various embodiments of the present invention provide a predictable method of referencing the PCL to prepare the proximal tibial cut. In various examples of the present invention the PCL-oriented instruments offer an advantage in that they may help ensure preservation of the integrity of the PCL. Another benefit that may be provided is the availability of tibial inserts with different slopes, enabling surgeons to optimize PCL tension and restore the knee joint line.

In another example, a PCL referencing method may be associated with determining a required tibial insert (and/or tibial insert trial) slope and/or producing a required tibial insert (and/or tibial insert trial) slope.

In another example, a tibial cut may be based (at least in part) on the location of the PCL tibial attachment.

In another example, an instrument may be provided for referencing the PCL tibial attachment.

In another embodiment, a knee prosthesis system is provided, comprising: at least a first tibial component, wherein the first tibial component has a first surface, a second surface, a length X along a first axis of the first tibial component, a width Y along a second axis of the first tibial component, and a thickness Z between the first surface of the first tibial component and the second surface of the first tibial component, wherein the first surface of the first tibial component is an articulation surface comprising at least one concave portion, wherein the thickness Z is between the second surface of the first tibial component and a low point of the concave portion of the first tibial component, wherein the first surface of the first tibial component is disposed on a slope relative to the second surface of the first tibial component and wherein the slope is defined by an angle A formed by: (a) a planar portion of the second surface of the first tibial component; and (b) a line connecting: (i) a highest point of the concave portion of first tibial component at an anterior end of the first tibial component and (ii) a highest point of the concave portion of the first tibial component at a posterior end of the first tibial component; at least a second tibial component, wherein the second tibial component has a first surface, a second surface, a length X along a first axis of the second tibial component, a width Y along a second axis of the second tibial component, and a thickness Z between the first surface of the second tibial component and the second surface of the second tibial component, wherein the first surface of the second tibial component is an articulation surface comprising at least one concave portion, wherein the thickness Z is between the second surface of the second tibial component and a low point of the concave portion of the second tibial component, wherein the first surface of the second tibial component is disposed on a slope relative to the second surface of the second tibial component and wherein the slope is defined by an angle A formed by: (a) a planar portion of the second surface of the second tibial component; and (b) a line connecting: (i) a highest point of the concave portion of second tibial component at an anterior end of the second tibial component and (ii) a highest point of the concave portion of the second tibial component at a posterior end of the second tibial component; wherein the thickness Z is substantially the same for both the first tibial component and the second tibial component; wherein the length X is substantially the same for both the first tibial component and the second tibial component; wherein the width Y is substantially the same for both the first tibial component and the second tibial component; and wherein the angle A of the first tibial component is different from the angle A of the second tibial component such that the slope of the first surface of the first tibial component is distinct from the slope of the first surface of the second tibial component.

In one example, the first tibial component may be a tibial insert and the second tibial component may be a tibial insert.

In another example, the first tibial component may comprise ultra high molecular weight polyethylene and the second tibial component may comprise ultra high molecular weight polyethylene.

In another example, the first tibial component may be a tibial insert trial and the second tibial component may be a tibial insert trial.

In another example, the first tibial component may comprise a copolymer and the second tibial component may comprise a copolymer.

In another example, the second surface of the first tibial component may be configured to interface with a tibial tray and the second surface of the second tibial component may be configured to interface with the tibial tray.

In another example, the concave portion of the articulation surface of the first tibial component may be configured to interface with a femoral component and the concave portion of the articulation surface of the second tibial component may be configured to interface with the femoral component.

In another example, the concave portion of the articulation surface of the first tibial component and the concave portion of the articulation surface of the second tibial component may have essentially the same congruency with the femoral component.

In another example, the concave portion of the articulation surface of the first tibial component and the concave portion of the articulation surface of the second tibial component may have essentially the same radius.

In another example, the first surface of the first tibial component may comprise a medial concave portion and a lateral concave portion and the first surface of the second tibial component may comprise a medial concave portion and a lateral concave portion.

In another embodiment, a knee prosthesis system is provided, comprising: n tibial components, wherein each of the n tibial components has a first surface, a second surface, a length X along a first axis of the respective tibial component, a width Y along a second axis of the respective tibial component, and a thickness Z between the first surface of the respective tibial component and the second surface of the respective tibial component, wherein the first surface of each of the n tibial components is an articulation surface comprising at least one concave portion, wherein the thickness Z is between the second surface of the respective tibial component and a low point of the concave portion of the respective tibial component, wherein the first surface of the respective tibial component is disposed on a slope relative to the second surface of the respective tibial component and wherein the slope is defined by an angle A formed by: (a) a planar portion of the second surface of the respective tibial component; and (b) a line connecting: (i) a highest point of the concave portion of the respective tibial component at an anterior end of the respective tibial component and (ii) a highest point of the concave portion of the respective tibial component at a posterior end of the respective tibial component; wherein the thickness Z is substantially the same for each of the n tibial components; wherein the length X is substantially the same for each of the n tibial components; wherein the width Y is substantially the same for each of the n tibial components; wherein the angle A each of the n tibial components is distinct from the angle A of each of the other n tibial components, such that the slope of the first surface of the each of the n tibial components is different from the slope of the first surface of each of the other n tibial components; and wherein n is an integer between 2 and 200.

In one example, n may be an integer between 2 and 45.

In another example, the system may further comprise: m tibial components, wherein each of the m tibial components has a first surface, a second surface, a length X' along a first axis of the respective tibial component, a width Y' along a second axis of the respective tibial component, and a thickness Z' between the first surface of the respective tibial component and the second surface of the respective tibial component, wherein the first surface of each of the m tibial components is an articulation surface comprising at least one concave portion, wherein the thickness Z' is between the second surface of the respective tibial component and a low point of the concave portion of the respective tibial component, wherein the first surface of the respective tibial component is disposed on a slope relative to the second surface of the respective tibial component and wherein the slope is defined by an angle A' formed by: (a) a planar portion of the second surface of the respective tibial component; and (b) a line connecting: (i) a highest point of the concave portion of the respective tibial component at an anterior end of the respective tibial component and (ii) a highest point of the concave portion of the respective tibial component at a posterior end of the respective tibial component; wherein the thickness Z' is substantially the same for each of the m tibial components; wherein the length X' is substantially the same for each of the m tibial components; wherein the width Y' is substantially the same for each of the m tibial components; wherein the angle A' each of the m tibial components is different from the angle A' each of the other m tibial components, such that the slope of the first surface of the each of the m tibial components is distinct from the slope of the first surface of each of the other m tibial components; wherein at least one of: (a) the thickness Z' of each of the m tibial components is different from the thickness Z of each of the n tibial components; (b) the length X' of each of the m tibial components is different from the length X of each of the n tibial components; and (c) the width Y' of each of the m tibial components is different from the width Y of each of the n tibial components; and wherein m is an integer between 2 and 200.

In another example: (a) the thickness Z' of each of the m tibial components is different from the thickness Z of each of the n tibial components; (b) the length X' of each of the m tibial components is different from the length X of each of the n tibial components; and (c) the width Y' of each of the m tibial components is different from the width Y of each of the n tibial components.

In another example: (a) the thickness Z' of each of the m tibial components is different from the thickness Z of each of the n tibial components; (b) the length X' of each of the m tibial components is essentially the same as the length X of each of the n tibial components; and (c) the width Y' of each of the m tibial components is essentially the same as from the width Y of each of the n tibial components.

In another example: (a) the thickness Z' of each of the m tibial components is essentially the same as the thickness Z of each of the n tibial components; (b) the length X' of each of the m tibial components is different from the length X of each of the n tibial components; and (c) the width Y' of each of the m tibial components is different from the width Y of each of the n tibial components.

In another example, m may be an integer between 2 and 45

In another example, at least one angle A' of at least one of the m tibial components may be essentially the same as at least one angle A of at least one of the n tibial components.

In another example, each angle A' of the m tibial components may be essentially the same as each angle A of a respective one of each of the n tibial components.

In another example, each of the n tibial components may be a tibial insert.

In another example, each of the n tibial components may be a tibial insert trial.

In another example, each of the m tibial components may be a tibial insert.

In another example, each of the m tibial components may be a tibial insert trial.

In another example, the second surface of each of the n tibial components may be configured to interface with a tibial tray.

In another example, the second surface of each of the m tibial components may be configured to interface with a tibial tray.

In another example, the concave portion of the articulation surface of each of the n tibial components may be configured to interface with a femoral component.

In another example, the concave portion of the articulation surface of each of the m tibial components may be configured to interface with a femoral component.

In another example, the concave portion of the articulation surface of each of the n tibial components may have essentially the same congruency with the femoral component.

In another example, the concave portion of the articulation surface of each of the m tibial components may have essentially the same congruency with the femoral component.

In another example, the concave portion of the articulation surface of each of the n tibial components may have essentially the same radius.

In another example, the concave portion of the articulation surface of each of the m tibial components may have essentially the same radius.

In another example, the first surface of each of the n tibial components may comprise a medial concave portion and a lateral concave portion.

In another example, the first surface of each of the m tibial components may comprise a medial concave portion and a lateral concave portion.

In another embodiment, an adjustable tibial insert trial is provided, comprising: a base, wherein the base comprises a first surface; a pivot mechanism; and a body portion, wherein the body portion comprises a first surface, wherein the first surface of the body portion is an articulation surface comprising at least one concave portion, and wherein the body portion is pivotally connected to the base; wherein the pivotal connection of the body portion to the base permits a slope of the body portion relative to the base to be adjusted; and wherein the slope is defined by an angle A formed by: (a) a planar portion of the first surface of the base; and (b) a line connecting: (i) a highest point of the concave portion of body portion at an anterior end of the body portion and (ii) a highest point of the concave portion of the body portion at a posterior end of the body portion.

In one example, the first surface of the base may be configured to interface with a tibial tray or a proximal tibial cut.

In another example, the concave portion of the articulation surface of the body portion may be configured to interface with a femoral component.

In another example, the first surface of the body portion may comprise a medial concave portion and a lateral concave portion.

In another example, the adjustable tibial insert trial may further comprise an adjustment mechanism for adjusting the slope of the body portion relative to the base.

In another example, the adjustment mechanism may comprise a screw.

In another embodiment, a surgical method for preparing a proximal tibia bone (e.g., a proximal portion of a tibia bone) of a patient is provided, comprising: determining a position of a proximate cruciate ligament attachment to the tibia bone; and cutting the proximal tibia bone at a position relative to the determined position of the proximate cruciate ligament attachment to the tibia bone.

In one example, the proximal tibia bone may be cut to provide a surface upon which a tibial tray is implanted.

In another example, the proximal tibia bone may be cut to form a substantially planar surface.

In another example, the proximal tibia bone may be cut at an angle relative to a long axis of the tibia bone, wherein the angle is a 90 degree angle.

In another example, the proximal tibia bone may be cut at an angle relative to a long axis of the tibia bone, wherein the angle is not a 90 degree angle.

In another embodiment, a surgical instrument is provided, wherein the surgical instrument is used with a tibial cutting block to prepare a proximal tibia bone of a patient, comprising: a body portion, wherein the body portion comprises at least one aperture therethrough; a stylus, wherein the stylus is elongated along a first axis, wherein the stylus comprises a tip which extends from the stylus at a non-zero angle relative to the first axis; and wherein the stylus is sized to fit through the aperture of the body portion such that the stylus is translatable along the first axis for at least a portion of stylus; a mount element, wherein the mount element is attached to the body portion and wherein the mount element is configured to be attached to the tibial cutting block; and a height adjustment mechanism, wherein the height adjustment mechanism is configured to change the height of the stylus relative to the mount element when the stylus is disposed in the aperture of the body portion.

In one example, the height adjustment mechanism may be configured to permit the stylus to be raised relative to the mount element.

In another example, the height adjustment mechanism may be configured to permit the stylus to be lowered relative to the mount element.

In another example, the body portion may comprise a mechanism for indicating the height of the stylus relative to the mount element.

In another example, the height adjustment mechanism may comprise a threaded interface controlled by a rotatable knob.

In another example, the surgical instrument may further comprise a pivot mechanism, wherein the pivot mechanism is associated with the mount element.

In another example, the pivot mechanism may permit the body portion to pivot relative to the tibial cutting block when the mount element is attached to the tibial cutting block.

In another example, the pivot mechanism may comprise a locking element which is configured to be selectively actuated to permit the body portion to pivot or to prohibit the body from pivoting.

In another example, the mount element may be removably attached to the tibial cutting block.

As described herein, under various embodiments of the present invention, after a tibial bone cut is made, a surgeon would not have to re-cut the tibial bone—the cut bone may be left as-is and various mechanisms may be provided to allow for a change in angularity (e.g., while holding thickness essentially constant). In one example, the mechanism may comprise tibial inserts/trials with several slope options.

Further, as described herein, under various embodiments of the present invention, instrumentation comprising a family of different tibial inserts/trials (e.g., at least two) may be provided (in one example, each of the tibial inserts/trials may have essentially the same articular geometry and only differ in slope).

Further, as described herein, under various embodiments of the present invention, instrumentation comprising a family of different tibial inserts/trials (e.g., at least two) may be provided (in one example, each of the tibial inserts/trials may have essentially the same backside (e.g., to fit to the same tibial tray) and articular geometry (e.g., congruence) in order to articulate with the same femoral component (the different tibial inserts/trials may differ in slope and/or size and/or thickness).

Further, as described herein, under various embodiments of the present invention, instrumentation comprising a family of different tibial inserts/trials (e.g., at least two) may be provided (in one example, for a given size and given thickness, a given articular geometry may be rotated around an axis (e.g., medial-lateral axis) and may or may not be translated (e.g., anterior-posterior).

While a number of embodiments of the present invention have been described, it is understood that these embodiments are illustrative only, and not restrictive, and that many modifications may become apparent to those of ordinary skill in the art. For example, any element described herein may be provided in any desired size (e.g., any element described herein may be provided in any desired custom size or any element described herein may be provided in any desired size selected from a "family" of sizes, such as small, medium, large). Further, one or more of the components may be made from any of the following materials: (a) any biocompatible material (which biocompatible material may be treated to permit surface bone ingrowth or prohibit surface bone ingrowth—depending upon the desire of the surgeon); (b) a plastic; (c) a fiber; (d) a polymer; (e) a metal (a pure metal such as titanium and/or an alloy such as Cobalt Chrome, Ti—Al—Nb, Ti-6Al-4V, stainless steel); (f) any combination thereof. Further still, any metal construct may be a machined metal construct. Further still, any number of protrusions (e.g., such as for initial fixation by forming a bond with cement and/or such as for supplemental fixation by forming a bond with cement) may be utilized with a given prosthesis. Further still, any number of female features that increase the cement mantle and/or provide an interlock may be utilized with a given prosthesis. Further still, any number of male features that could dig into the bone so that initial/supplemental fixation can be improved may be utilized with a given prosthesis. Further still, any number of bone screws (e.g., such as for initial fixation and/or such as for supplemental fixation) may be utilized with a given prosthesis. Further still, the implant (and/or trial) may comprise one or more dimples, indents, apertures, slots or the like for handling the implant (and/or trial) with a tool. Further still, the present invention is intended to encompass any methods for constructing and/or utilizing any systems and/or structures disclosed herein. Further still, any steps described herein may be carried out in any desired order (and any additional steps may be added as desired and/or any steps may be deleted as desired).

What is claimed is:

1. A knee prosthesis system, comprising:
   at least a first tibial component, wherein the first tibial component has a first surface comprising a medial concave articulation surface and a lateral concave articulation surface, a second surface, a length X along a first axis of the first tibial component, a width Y along a second axis of the first tibial component, and a thickness Z between the first surface of the first tibial component and the second surface of the first tibial component, wherein the thickness Z is located in the transverse plane and is between the second surface of the first tibial component and the lowest point of the concave articulation surfaces of the first tibial component, wherein the medial concave articulation surface and the lateral concave articulation surface of the first tibial component are each defined by a first tibial insert slope that is equal;
   at least a second tibial component, wherein the second tibial component has a first surface comprising a medial concave articulation surface and a lateral concave articulation surface, a second surface, a length X along a first axis of the second tibial component, a width Y along a second axis of the second tibial component, and a thickness Z between the first surface of the second tibial component and the second surface of the second tibial component, wherein the thickness Z is located in the transverse plane and is between the second surface of the second tibial component and the lowest point of the concave articulation surfaces of the second tibial component, wherein the medial concave articulation surface and the lateral concave articulation surface of the second tibial component are each defined by a first tibial insert slope that is equal;
   wherein the thickness Z is substantially the same for both the first tibial component and the second tibial component;
   wherein the length X is substantially the same for both the first tibial component and the second tibial component;
   wherein the width Y is substantially the same for both the first tibial component and the second tibial component; and
   wherein the first tibial insert slope is different than the second tibial insert slope.

2. The system of claim 1, wherein the first tibial component is a tibial insert and wherein the second tibial component is a tibial insert.

3. The system of claim 2, wherein the first tibial component comprises ultra high molecular weight polyethylene and wherein the second tibial component comprises ultra high molecular weight polyethylene.

4. The system of claim 1, wherein the first tibial component is a tibial insert trial and wherein the second tibial component is a tibial insert trial.

5. The system of claim 4, wherein the first tibial component comprises a copolymer and wherein the second tibial component comprises a copolymer.

6. The system of claim 1, wherein the second surface of the first tibial component is configured to interface with a tibial tray and wherein the second surface of the second tibial component is configured to interface with the tibial tray.

7. The system of claim 1, wherein the concave articulation surfaces of the first tibial component are configured to interface with a femoral component and wherein the concave articulation surfaces of the second tibial component is configured to interface with the femoral component.

8. The system of claim 7, wherein the concave articulation surfaces of the first tibial component and the concave articulation surfaces of the second tibial component have essentially the same congruency with the femoral component.

9. The system of claim 1, wherein the concave articulation surfaces of the first tibial component and the concave articulation surfaces of the second tibial component have essentially the same radius.

10. The system of claim 1 further comprising:
    at least a third tibial component, wherein the third tibial component has a first surface comprising a medial concave articulation surface and a lateral concave articulation surface, a second surface, a length X along a first axis of the third tibial component, a width Y along a second axis of the third tibial component, and a thickness Z between the first surface of the third tibial component and the second surface of the third tibial component, wherein the thickness Z is located in the transverse plane and is between the second surface of the third tibial component and the lowest point of the concave articulation surfaces of the third tibial component, wherein the medial concave articulation surface and the lateral concave articulation surface of the third tibial component are each defined by a third tibial insert slope that is equal;

wherein the thickness Z is substantially the same for the first tibial component, the second tibial component, and the third tibial component;

wherein the length X is substantially the same for the first tibial component, the second tibial component, and the third tibial component;

wherein the width Y is substantially the same for the first tibial component, the second tibial component, and the third tibial component; and wherein the first tibial insert slope, the second tibial insert slope, and the third tibial insert slope are each different from one another.

11. The system of claim 10, wherein the third tibial component is a tibial insert.

12. The system of claim 10, wherein the third tibial component comprises ultra high molecular weight polyethylene.

13. The system of claim 10, wherein the third tibial component is a tibial insert trial.

14. The system of claim 10, wherein the third tibial component comprises a copolymer.

15. The system of claim 10, wherein the second surface of the third tibial component is configured to interface with a tibial tray.

16. The system of claim 10, wherein the concave articulation surfaces of the third tibial component are configured to interface with a femoral component.

17. The system of claim 10, wherein the concave articulation surfaces of the third tibial component, the concave articulation surfaces of the second tibial component, and the concave articulation surfaces of the first tibial component have essentially the same congruency with a femoral component.

18. The system of claim 10, wherein the concave articulation surfaces of the third tibial component, the concave articulation surfaces of the second tibial component, and the concave articulation surfaces of the first tibial component have essentially the same radius.

* * * * *